(12) United States Patent
Behzadi

(10) Patent No.: US 11,331,069 B2
(45) Date of Patent: *May 17, 2022

(54) INVASIVE SENSE MEASUREMENT IN PROSTHESIS INSTALLATION

(71) Applicant: Kambiz Behzadi, Pleasanton, CA (US)

(72) Inventor: Kambiz Behzadi, Pleasanton, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 16/571,180

(22) Filed: Sep. 15, 2019

(65) Prior Publication Data

US 2020/0008774 A1 Jan. 9, 2020

Related U.S. Application Data

(63) Continuation of application No. 15/284,091, filed on Oct. 3, 2016, now Pat. No. 10,441,244, which is a continuation-in-part of application No. 15/234,782, filed on Aug. 11, 2016, now Pat. No. 10,912,655, which is a continuation-in-part of application No. 15/202,434, filed on Jul. 5, 2016, now abandoned.

(Continued)

(51) Int. Cl.
*A61F 2/46* (2006.01)
*A61B 7/02* (2006.01)
*A61F 2/34* (2006.01)
*A61B 90/00* (2016.01)

(52) U.S. Cl.
CPC ............... *A61B 7/023* (2013.01); *A61F 2/34* (2013.01); *A61F 2/468* (2013.01); *A61B 2090/064* (2016.02)

(58) Field of Classification Search
CPC .......... A61F 2/46; A61F 2/4607; A61F 2/468; A61B 17/1666; A61B 7/023; A61B 5/4851
See application file for complete search history.

(56) References Cited

U.S. PATENT DOCUMENTS

| | | | |
|---|---|---|---|
| 1,455,621 | A | 5/1923 | Joyner |
| 2,121,193 | A | 6/1938 | Hanicke |
| 3,818,514 | A | 6/1974 | Clark |
| 3,874,003 | A | 4/1975 | Moser et al. |
| 4,135,517 | A | 1/1979 | Reale |
| 4,301,551 | A | 11/1981 | Dore et al. |
| 4,457,306 | A | 7/1984 | Borzone |

(Continued)

FOREIGN PATENT DOCUMENTS

| | | |
|---|---|---|
| EP | 1433445 A1 | 6/2004 |
| WO | 2007096476 A2 | 8/2007 |

(Continued)

OTHER PUBLICATIONS

International Search Report for International application No. PCT/US2017/012753, dated May 5, 2017.

(Continued)

*Primary Examiner* — Si Ming Ku
(74) *Attorney, Agent, or Firm* — Patent Law Offices of Michael E. Woods; Michael Woods

(57) ABSTRACT

A system and method for allowing any surgeon, including those surgeons who perform a fewer number of a replacement procedure as compared to a more experienced surgeon who performs a greater number of procedures, to provide an improved likelihood of a favorable outcome approaching, if not exceeding, a likelihood of a favorable outcome as performed by a very experienced surgeon with the replacement procedure. Force sensing is included to aid in quantifying installation of an implant, particularly a cup into a pelvic bone.

20 Claims, 28 Drawing Sheets

Related U.S. Application Data

(60) Provisional application No. 62/277,294, filed on Jan. 11, 2016, provisional application No. 62/355,657, filed on Jun. 28, 2016, provisional application No. 62/353,024, filed on Jun. 21, 2016.

(56) References Cited

U.S. PATENT DOCUMENTS

| | | |
|---|---|---|
| 4,530,114 A | 7/1985 | Tepic |
| 4,608,019 A | 8/1986 | Kumabe et al. |
| 4,608,053 A | 8/1986 | Keller |
| 4,712,951 A | 12/1987 | Brown |
| 4,728,329 A | 3/1988 | Mansat |
| 5,108,400 A | 4/1992 | Appel et al. |
| 5,133,765 A | 7/1992 | Cuilleron |
| 5,318,570 A | 6/1994 | Hood et al. |
| 5,358,532 A | 10/1994 | Evans et al. |
| 5,431,657 A | 7/1995 | Rohr |
| 5,534,006 A | 7/1996 | Szabo et al. |
| 5,591,164 A | 1/1997 | Nazre et al. |
| 5,665,091 A | 9/1997 | Noble et al. |
| 5,693,088 A | 12/1997 | Lazarus |
| 5,702,473 A | 12/1997 | Albrektsson et al. |
| 5,713,901 A | 2/1998 | Tock |
| 5,769,092 A | 6/1998 | Williamson, Jr. |
| 5,806,518 A | 9/1998 | Mittelstadt |
| 5,849,015 A | 12/1998 | Haywood et al. |
| 5,980,528 A | 11/1999 | Salys |
| 6,048,365 A | 4/2000 | Burrows et al. |
| 6,110,179 A | 8/2000 | Flivik et al. |
| 6,146,425 A | 11/2000 | Hoermansdoerfer |
| 6,161,545 A | 12/2000 | Chow |
| 6,197,062 B1 | 3/2001 | Fenlin |
| 6,204,592 B1 | 3/2001 | Hur |
| 6,231,612 B1 | 5/2001 | Balay et al. |
| 6,585,771 B1 | 7/2003 | Buttermilch et al. |
| 7,036,211 B1 | 5/2006 | Panks |
| 7,645,281 B2 | 1/2010 | Marik |
| 7,875,083 B2 | 1/2011 | Sudmann |
| 8,167,823 B2 | 5/2012 | Nycz et al. |
| 8,328,849 B2 | 12/2012 | Nydegger et al. |
| 8,603,100 B2 | 12/2013 | Muller |
| 8,876,529 B2 | 11/2014 | Mayer et al. |
| 9,232,968 B2 | 1/2016 | Moumene et al. |
| 9,999,518 B2 | 6/2018 | Mani et al. |
| 10,251,663 B2 | 4/2019 | Behzadi |
| 10,299,930 B2 | 5/2019 | Behzadi |
| 10,849,766 B2 | 12/2020 | Behzadi |
| 10,864,083 B2 | 12/2020 | Behzadi |
| 10,905,456 B2 | 2/2021 | Behzadi |
| 10,912,655 B2 | 2/2021 | Behzadi et al. |
| 11,026,809 B2 | 6/2021 | Behzadi et al. |
| 2002/0082695 A1 | 6/2002 | Neumann |
| 2002/0183851 A1 | 12/2002 | Spiegelberg et al. |
| 2003/0065398 A1 | 4/2003 | Cueille et al. |
| 2003/0229357 A1 | 12/2003 | Dye |
| 2004/0019382 A1 | 1/2004 | Amirouche et al. |
| 2004/0044397 A1 | 3/2004 | Stinson |
| 2004/0097952 A1 | 5/2004 | Sarin et al. |
| 2005/0004680 A1 | 1/2005 | Saladino et al. |
| 2005/0015154 A1 | 1/2005 | Lindsey et al. |
| 2005/0101962 A1 | 5/2005 | Schwenke et al. |
| 2005/0154398 A1 | 7/2005 | Miniaci et al. |
| 2005/0209597 A1 | 9/2005 | Long et al. |
| 2006/0015110 A1 | 1/2006 | Pepper |
| 2006/0142754 A1 | 6/2006 | Irion et al. |
| 2006/0247638 A1 | 11/2006 | Trieu et al. |
| 2007/0005144 A1 | 1/2007 | Leisinger et al. |
| 2007/0162038 A1 | 7/2007 | Tuke |
| 2007/0219641 A1 | 9/2007 | Dorr et al. |
| 2007/0233131 A1 | 10/2007 | Song et al. |
| 2008/0091271 A1 | 4/2008 | Bonitati et al. |
| 2008/0109085 A1 | 5/2008 | Tulkis et al. |
| 2008/0234833 A1 | 9/2008 | Bandoh et al. |
| 2008/0255560 A1 | 10/2008 | Myers et al. |
| 2009/0112265 A1 | 4/2009 | Hudgins et al. |
| 2009/0192626 A1 | 7/2009 | Keefer et al. |
| 2009/0248083 A1 | 10/2009 | Patterson et al. |
| 2009/0292321 A1 | 11/2009 | Collette |
| 2010/0023014 A1 | 1/2010 | Romagnoli et al. |
| 2010/0249796 A1* | 9/2010 | Nycz ............... A61F 2/4657 606/99 |
| 2011/0004318 A1 | 1/2011 | Tulkis et al. |
| 2011/0178521 A1 | 7/2011 | Siravo et al. |
| 2011/0264009 A1 | 10/2011 | Walter et al. |
| 2012/0172939 A1 | 7/2012 | Pedicini |
| 2012/0209277 A1 | 8/2012 | Leparmentier et al. |
| 2013/0204264 A1 | 8/2013 | Mani et al. |
| 2013/0211535 A1 | 8/2013 | Cueille |
| 2013/0226189 A1 | 8/2013 | Young |
| 2013/0261762 A1 | 10/2013 | Kennedy |
| 2014/0012391 A1 | 1/2014 | Gugler et al. |
| 2014/0058526 A1 | 2/2014 | Meridew et al. |
| 2014/0128986 A1 | 5/2014 | Podolsky |
| 2014/0135773 A1 | 5/2014 | Stein et al. |
| 2014/0135791 A1 | 5/2014 | Nikou et al. |
| 2014/0207123 A1 | 7/2014 | Mueller |
| 2014/0257293 A1 | 9/2014 | Axelson, Jr. et al. |
| 2014/0303743 A1 | 10/2014 | Choudhury et al. |
| 2014/0330281 A1 | 11/2014 | Aghazadeh |
| 2014/0363481 A1 | 12/2014 | Pasini et al. |
| 2014/0370462 A1 | 12/2014 | Porter et al. |
| 2014/0371897 A1 | 12/2014 | Lin et al. |
| 2015/0182350 A1 | 7/2015 | Behzadi |
| 2015/0182351 A1 | 7/2015 | Behzadi |
| 2015/0196343 A1 | 7/2015 | Donald et al. |
| 2015/0201918 A1 | 7/2015 | Kumar et al. |
| 2015/0216668 A1 | 8/2015 | Smith |
| 2015/0282856 A1 | 10/2015 | Haiat et al. |
| 2016/0029952 A1 | 2/2016 | Hunter |
| 2016/0058519 A1 | 3/2016 | Herr |
| 2016/0166390 A1 | 6/2016 | Dye et al. |
| 2016/0206430 A1 | 7/2016 | Grostefon et al. |
| 2016/0206433 A1 | 7/2016 | Grostefon et al. |
| 2016/0220315 A1 | 8/2016 | Falardeau et al. |
| 2016/0338751 A1 | 11/2016 | Kellar et al. |
| 2017/0056205 A1 | 3/2017 | Biegun et al. |
| 2017/0196506 A1 | 7/2017 | Behzadi |
| 2017/0196701 A1 | 7/2017 | Behzadi et al. |
| 2017/0196704 A1 | 7/2017 | Behzadi et al. |
| 2017/0196705 A1 | 7/2017 | Behzadi |
| 2017/0196706 A1 | 7/2017 | Behzadi |
| 2017/0196707 A1 | 7/2017 | Behzadi |
| 2017/0196708 A1 | 7/2017 | Behzadi et al. |
| 2017/0196710 A1 | 7/2017 | Behzadi |
| 2017/0196711 A1 | 7/2017 | Behzadi |
| 2017/0290666 A1 | 10/2017 | Behzadi |
| 2017/0290667 A1 | 10/2017 | Behzadi |
| 2017/0325972 A1 | 11/2017 | Steif |
| 2017/0340448 A1 | 11/2017 | Behzadi |
| 2017/0340456 A1 | 11/2017 | Behzadi |
| 2017/0354505 A1 | 12/2017 | Behzadi |
| 2018/0049891 A1 | 2/2018 | Termanini |
| 2018/0235764 A1 | 8/2018 | Moore et al. |
| 2018/0235765 A1 | 8/2018 | Welker et al. |
| 2018/0296364 A1 | 10/2018 | Harris et al. |
| 2018/0325695 A1 | 11/2018 | Wozencroft |
| 2019/0336307 A1 | 11/2019 | Sungu et al. |
| 2020/0069279 A1 | 3/2020 | Behzadi et al. |
| 2020/0069280 A1 | 3/2020 | Behzadi et al. |
| 2020/0205988 A1 | 7/2020 | Behzadi et al. |
| 2020/0261232 A1 | 8/2020 | Mistry |
| 2020/0297499 A1 | 9/2020 | Behzadi et al. |

FOREIGN PATENT DOCUMENTS

| | | |
|---|---|---|
| WO | 2017029173 A1 | 2/2017 |
| WO | 2018031752 A1 | 2/2018 |

OTHER PUBLICATIONS

Written Opinion of the International Searching Authority for International application No. PCT/US2017/012753 dated May 5, 2017.

(56) References Cited

OTHER PUBLICATIONS

International Search Report for International application No. PCT/US2017/046261, dated Oct. 18, 2017.
Written Opinion of the International Searching Authority for International application No. PCT/US2017/046261, dated Oct. 18, 2017.
PCT International Search Report for International application No. PCT/US17/26417, dated Jul. 3, 2017.
PCT Written Opinion of The International Searching Authority for International application No. PCT/US17/26417 dated Jul. 3, 2017.
International Search Report regarding International application No. PCT/US2017/037042 dated Oct. 6, 2017.
Written Opinion of the International Searching Authority regarding International application No. PCT/US2017/037042 dated Oct. 6, 2017.

\* cited by examiner

INVASIVE SENSE MEASUREMENT IN PROSTHESIS INSTALLATION

CROSS REFERENCE TO RELATED APPLICATIONS

This application is a Continuation of application Ser. No. 15/284,091 filed on Oct. 3, 2016, application Ser. No. 15/284,091 is a Continuation-in-part of application Ser. No. 15/234,782 filed on Aug. 11, 2016, application Ser. No. 15/234,782 is a Continuation-in-part of application Ser. No. 15/202,434 filed on Jul. 5, 2016, Application Ser. No. 15/202,434 claims the benefit of U.S. Provisional Application 62/277,294 filed on Jan. 11, 2016, application Ser. No. 15/234,782 claims the benefit of U.S. Provisional Application 62/355,657 filed on Jun. 28, 2016, application Ser. No. 15/234,782 claims the benefit of U.S. Provisional Application 62/353,024 filed on Jun. 21, 2016, the contents of each of these applications in their entireties are hereby expressly incorporated by reference thereto for all purposes.

FIELD OF THE INVENTION

The present invention relates generally to orthopedic surgical systems and procedures employing a prosthetic implant for, and more specifically, but not exclusively, to joint replacement therapies such as total hip replacement including controlled installation and positioning of the prosthesis such as during replacement of a pelvic acetabulum with a prosthetic implant, and relates generally to installation of a prosthesis, and more specifically, but not exclusively, to improvements in prosthesis placement and positioning, and relates generally to force measurement systems such as may be used in these systems and methods.

BACKGROUND OF THE INVENTION

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Total hip replacement refers to a surgical procedure where a hip joint is replaced using a prosthetic implant. There are several different techniques that may be used, but all include a step of inserting an acetabular component into the acetabulum and positioning it correctly in three dimensions (along an X, Y, and Z axis).

In total hip replacement (THR) procedures there are advantages to patient outcome when the procedure is performed by a surgeon specializing in these procedures. Patients of surgeons who do not perform as many procedures can have increased risks of complications, particularly of complications arising from incorrect placement and positioning of the acetabular component.

The incorrect placement and positioning may arise even when the surgeon understood and intended the acetabular component to be inserted and positioned correctly. This is true because in some techniques, the tools for actually installing the acetabular component are crude and provide an imprecise, unpredictable coarse positioning outcome.

It is known in some techniques to employ automated and/or computer-assisted navigation tools, for example, x-ray fluoroscopy or computer guidance systems. There are computer assisted surgery techniques that can help the surgeon in determining the correct orientation and placement of the acetabular component. However, current technology provides that at some point the surgeon is required to employ a hammer/mallet to physically strike a pin or alignment rod. The amount of force applied and the location of the application of the force are variables that have not been controlled by these navigation tools. Thus, even when the acetabular component is properly positioned and oriented, when actually impacting the acetabular component into place the actual location and orientation can differ from the intended optimum location and orientation. In some cases, the tools used can be used to determine that there is, in fact, some difference in the location and/or orientation. However, once again the surgeon must employ an impacting tool (e.g., the hammer/mallet) to strike the pin or alignment rod to attempt an adjustment. However, the resulting location and orientation of the acetabular component after the adjustment may not be, in fact, the desired location and/or orientation. The more familiar that the surgeon is with the use and application of these adjustment tools can reduce the risk to a patient from a less preferred location or orientation. In some circumstances, quite large impacting forces are applied to the prosthesis by the mallet striking the rod; these forces make fine tuning difficult at best and there is risk of fracturing and/or shattering the acetabulum during these impacting steps.

Earlier patents issued to the present applicant have described problems associated with prosthesis installation, for example acetabular cup placement in total hip replacement surgery. See U.S. Pat. Nos. 9,168,154 and 9,220,612, which are hereby expressly incorporated by reference thereto in their entireties for all purposes. Even though hip replacement surgery has been one of the most successful operations, it continues to be plagued with a problem of inconsistent acetabular cup placement. Cup mal-positioning is the single greatest cause of hip instability, a major factor in polyethylene wear, osteolysis, impingement, component loosening and the need for hip revision surgery.

These incorporated patents explain that the process of cup implantation with a mallet is highly unreliable and a significant cause of this inconsistency. The patents note two specific problems associated with the use of the mallet. First is the fact that the surgeon is unable to consistently hit on the center point of the impaction plate, which causes undesirable torques and moment arms, leading to mal-alignment of the cup. Second, is the fact that the amount of force utilized in this process is non-standardized.

Traditionally these methods do not have any clear understanding of the forces, including magnitude and direction, involved in installing a prosthesis. A surgeon often relies on qualitative factors from tactile and auditory senses. Consequently, the surgeon is left somewhat haphazardly and variably relying on two different fixation methods (e.g., pins and press-fit) without knowing how or why.

In these patents there is presented a new apparatus and method of cup insertion which uses an oscillatory motion to insert the prosthesis. Prototypes have been developed and continue to be refined, and illustrate that vibratory force may allow insertion of the prosthesis with less force, as well, in some embodiments, of allowing simultaneous positioning and alignment of the implant.

There are other ways of breaking down of the large undesirable, torque-producing forces associated with the discrete blows of the mallet into a series of smaller, axially aligned controlled taps, which may achieve the same result incrementally, and in a stepwise fashion to those set forth in the incorporated patents, (with regard to, for example, cup insertion without unintended divergence).

There are two problems that may be considered independently, though some solutions may address both in a single solution. These problems include i) undesirable and unpredictable torques and moment arms that are related to the primitive method currently used by surgeons, which involves manually banging the mallet on an impaction plate mated to the prosthesis and ii) non-standardized and essentially uncontrolled and unquantized amounts of force utilized in these processes.

Total hip replacement has been one of the most successful orthopedic operations. However, as has been previously described in the incorporated applications, it continues to be plagued with the problem of inconsistent acetabular cup placement. Cup mal-positioning is a significant cause of hip instability, a major factor in polyethylene wear, osteolysis, impingement, component loosening, and the need for hip revision surgery.

Solutions in the incorporated applications generally relate to particular solutions that may not, in every situation and implementation, achieve desired goal(s) of a surgeon.

There are various sensing systems that may be used over a course of preparation and installation of a prosthesis, for example an acetabular cup. These sensing systems may detect various parameters such as an orientation angle of the prosthesis at any given time. These sensing systems may provide a set of periodic snapshots in time over the course of the procedure, but they do not provide true real-time continuous data over the installation procedure. That is, a surgeon may employ a sensing system to measure an orientation before striking an acetabular cup using a mallet and tamp, and may employ a sensing system to measure an orientation after striking the acetabular cup. But these sensing systems do not provide an orientation measurement (and in most cases no measurement of any information) during the strike. That is, the surgeon often measures, strikes, remeasures, restrikes, and repeats until the surgeon decides to stop. For a conventional system in which the surgeon manually swings the mallet and the installation model includes a sequence of discrete impulses from the mallet, this paradigm is understandable.

Some conventional systems may describe some measurements as "real time" but those systems are real time in the sense that the measurements are taken in the operating room during a procedure. The actual system does not provide real-time measurement during the actual insertion event.

In the incorporated applications, alternatives to the manual swinging of the mallet are described and in these systems the conventional measurement paradigm may be unnecessarily restrictive.

What is needed is a system and method for allowing any surgeon, including those surgeons who perform a fewer number of a replacement procedure as compared to a more experienced surgeon who performs a greater number of procedures, to provide an improved likelihood of a favorable outcome approaching, if not exceeding, a likelihood of a favorable outcome as performed by a very experienced surgeon with the replacement procedure, such as by understanding the prosthesis installation environment (e.g., cup/cavity interface) and to provide intelligent and interactive tools and methods to standardize the installation process.

BRIEF SUMMARY OF THE INVENTION

Disclosed is a system and method for allowing any surgeon, including those surgeons who perform a fewer number of a replacement procedure as compared to a more experienced surgeon who performs a greater number of procedures, to provide an improved likelihood of a favorable outcome approaching, if not exceeding, a likelihood of a favorable outcome as performed by a very experienced surgeon with the replacement procedure, such as by understanding the prosthesis installation environment (e.g., cup/cavity interface) and to provide intelligent and interactive tools and methods to standardize the installation process.

The following summary of the invention is provided to facilitate an understanding of some of technical features related to total hip replacement, and is not intended to be a full description of the present invention. A full appreciation of the various aspects of the invention can be gained by taking the entire specification, claims, drawings, and abstract as a whole. The present invention is applicable to other surgical procedures, including replacement of other joints replaced by a prosthetic implant in addition to replacement of an acetabulum (hip socket) with an acetabular component (e.g., a cup). Use of pneumatic and electric motor implementations have both achieved a proof of concept development.

The disclosed concepts involve creation of a system/method/tool/gun that vibrates an attached prosthesis, e.g., an acetabular cup. The gun would be held in a surgeon's hands and deployed. It would use a vibratory energy to insert (not impact) and position the cup into desired alignment (using current intra-operation measurement systems, navigation, fluoroscopy, and the like).

In one embodiment, a first gun-like device is used for accurate impaction of the acetabular component at the desired location and orientation.

In another embodiment, a second gun-like device is used for fine-tuning of the orientation of the acetabular component, such as one installed by the first gun-like device, by traditional mallet and tamp, or by other methodology. However, the second gun-like device may be used independently of the first gun-like device for adjusting an acetabular component installed using an alternate technique. Similarly, the second gun-like device may be used independently of the first gun-like device, particularly when the initial installation is sufficiently close to the desired location and orientation. These embodiments are not necessarily limited to fine-tuning as certain embodiments permit complete re-orientation. Some implementations allow for removal of an installed prosthesis.

Another embodiment includes a third gun-like device that combines the functions of the first gun-like device and the second gun-like device. This embodiment enables the surgeon to accurately locate, insert, orient, and otherwise position the acetabular component with the single tool.

Another embodiment includes a fourth device that installs the acetabular component without use of the mallet and the rod, or use of alternatives to strike the acetabular component for impacting it into the acetabulum. This embodiment imparts a vibratory motion to an installation rod coupled to the acetabular component that enables low-force, impactless installation and/or positioning.

An embodiment of the present invention may include axial alignment of force transference, such as, for example, an axially sliding hammer moving between stops to impart a non-torqueing installation force. There are various ways of motivating and controlling the sliding hammer, including a magnitude of transferred force. Optional enhancements may include pressure and/or sound sensors for gauging when a desired depth of implantation has occurred.

Other embodiments include adaptation of various devices for accurate assembly of modular prostheses, such as those that include a head accurately impacted onto a trunnion taper that is part of a stem or other element of the prosthesis.

Additional embodiments of the present invention may include a hybrid medical device that is capable of selectively using vibratory and/or axial-impacts at various phases of an installation as required, needed, and/or desired by the surgeon during a procedure. The single tool remains coupled to the prosthesis or prosthesis component as the surgeon operates the hybrid medical device in any of its phases, which include a pure vibratory mode, a pure axial mode, a blended vibratory and impactful mode. The axial impacts in this device may have sub-modes: a) unidirectional axial force-IN, b) unidirectional axial force-OUT, or c) bidirectional axial force.

An embodiment of the present invention may include true real-time sensing before, during, and after a procedure. These procedures may benefit from this invasive sensing (sensing during preparation of bone, during installation of a prosthesis, and during assembly of a modular prosthesis) and not just periodic static snapshots. The invasive sensing may employ force sensing directly, or may employ acceleration, vibration, or acoustic sensing in addition to, or in lieu of, force sensing.

A positioning device for an acetabular cup disposed in a bone, the acetabular cup including an outer shell having a sidewall defining an inner cavity and an opening with the sidewall having a periphery around the opening and with the acetabular cup having a desired abduction angle relative to the bone and a desired anteversion angle relative to the bone, including a controller including a trigger and a selector; a support having a proximal end and a distal end opposite of the proximal end, the support further having a longitudinal axis extending from the proximal end to the distal end with the proximal end coupled to the controller, the support further having an adapter coupled to the distal end with the adapter configured to secure the acetabular cup; and a number N, the number N, an integer greater than or equal to 2, of longitudinal actuators coupled to the controller and disposed around the support generally parallel to the longitudinal axis, each the actuator including an associated impact head arranged to strike a portion of the periphery, each impact head providing an impact strike to a different portion of the periphery when the associated actuator is selected and triggered; wherein each the impact strike adjusts one of the angles relative to the bone.

An installation device for an acetabular cup disposed in a pelvic bone, the acetabular cup including an outer shell having a sidewall defining an inner cavity and an opening with the sidewall having a periphery around the opening and with the acetabular cup having a desired installation depth relative to the bone, a desired abduction angle relative to the bone, and a desired anteversion angle relative to the bone, including a controller including a trigger; a support having a proximal end and a distal end opposite of said proximal end, said support further having a longitudinal axis extending from said proximal end to said distal end with said proximal end coupled to said controller, said support further having an adapter coupled to said distal end with said adapter configured to secure the acetabular cup; and an oscillator coupled to said controller and to said support, said oscillator configured to control an oscillation frequency and an oscillation magnitude of said support with said oscillation frequency and said oscillation magnitude configured to install the acetabular cup at the installation depth with the desired abduction angle and the desired anteversion angle without use of an impact force applied to the acetabular cup.

An installation system for a prosthesis configured to be implanted into a portion of bone at a desired implantation depth, the prosthesis including an attachment system, including an oscillation engine including a controller coupled to a vibratory machine generating an original series of pulses having a generation pattern, said generation pattern defining a first duty cycle of said original series of pulses; and a pulse transfer assembly having a proximal end coupled to said oscillation engine and a distal end, spaced from said proximal end, coupled to the prosthesis with said pulse transfer assembly including a connector system at said proximal end, said connector system complementary to the attachment system and configured to secure and rigidly hold the prosthesis producing a secured prosthesis with said pulse transfer assembly communicating an installation series of pulses, responsive to said original series of pulses, to said secured prosthesis producing an applied series of pulses responsive to said installation series of pulses; wherein said applied series of pulses are configured to impart a vibratory motion to said secured prosthesis enabling an installation of said secured prosthesis into the portion of bone to within 95% of the desired implantation depth without a manual impact.

A method for installing an acetabular cup into a prepared socket in a pelvic bone, the acetabular cup including an outer shell having a sidewall defining an inner cavity and an opening with the sidewall having a periphery around the opening and with the acetabular cup having a desired installation depth relative to the bone, a desired abduction angle relative to the bone, and a desired anteversion angle relative to the bone, including (a) generating an original series of pulses from an oscillation engine; (b) communicating said original series of pulses to the acetabular cup producing a communicated series of pulses at said acetabular cup; (c) vibrating, responsive to said communicated series of pulses, the acetabular cup to produce a vibrating acetabular cup having a predetermined vibration pattern; and (d) inserting the vibrating acetabular cup into the prepared socket within a first predefined threshold of the installation depth with the desired abduction angle and the desired anteversion angle without use of an impact force applied to the acetabular cup.

This method may further include (e) orienting the vibrating acetabular cup within the prepared socket within a second predetermined threshold of the desired abduction angle and within third predetermined threshold of the desired anteversion angle.

A method for inserting a prosthesis into a prepared location in a bone of a patient at a desired insertion depth wherein non-vibratory insertion forces for inserting the prosthesis to the desired insertion depth are in a first range, the method including (a) vibrating the prosthesis using a tool to produce a vibrating prosthesis having a predetermined vibration pattern; and (b) inserting the vibrating prosthesis into the prepared location to within a first predetermined threshold of the desired insertion depth using vibratory insertion forces in a second range, said second range including a set of values less than a lowest value of the first range.

An embodiment may include a force sensing system within the BMD tools with capacity to measure the force experienced by the system (mIF) (Within the tool) and calculate the change in mIF with respect to time, number of impacts, or depth of insertion. This system provides a feedback mechanism through the BMD tools, for the surgeon, as to when impaction should stop, and or if it should continue. This feedback mechanism can be created by measuring and calculating force, acceleration or insertion depth. In some implementations, an applied force is measured (TmIF) and compared against the mIF in any of several possible ways and an evaluation is made as to whether the prosthesis has stopped moving responsive to the applied forces. There are different implications depending upon where in the installation process the system is operating. In other implementations, the applied force is known or estimated and then the mIF may need to be measured.

An aspect of the present invention is use of a special version of this system to map out ranges of parameters for different prosthesis/cavity interactions to allow better understanding of typical or applicable curve for a particular patient with a particular implant procedure.

A force sensing system for a medical device tools with capacity to measure the force experienced by the system (mIF)—(Within the tool) and calculate a change in mIF with respect to time, number of impacts, or depth of insertion, wherein this system provides a feedback mechanism through the device, for the surgeon, as to when impaction should stop, and/or whether it should continue while assessing a risk of too early suspension with poor seating or too late when bone fracture risk is high and wherein this feedback mechanism can be created by measuring and calculating force, acceleration or insertion depth, among other variables.

An apparatus, including a medical device operating over a continuous period including an initial act with the medical device to a subsequent act with the medical device; and a microelectromechanical (MEM) sensing system physically coupled to the medical device configured to provide a real-time parametric evaluation over the period.

Any of the embodiments described herein may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Other features, benefits, and advantages of the present invention will be apparent upon a review of the present disclosure, including the specification, drawings, and claims.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

FIG. 7 illustrates a representative installation system;

FIG. 8 illustrates a disassembly of the representative installation system of FIG. 7;

FIG. 9 illustrates a first disassembly view of the pulse transfer assembly of the installation system of FIG. 7;

FIG. 10 illustrates a second disassembly view of the pulse transfer assembly of the installation system of FIG. 7;

FIG. 13 illustrates an initial engagement of a prosthesis to a cavity when the prosthesis is secured to a force sensing tool;

FIG. 14 illustrates a partial installation of the prosthesis of FIG. 13 into the cavity by operation of the force sensing tool;

FIG. 16 illustrates a representative plot of insertion force for a cup during installation;

FIG. 17 illustrates a first particular embodiment of a BMDX force sensing tool;

FIG. 18 illustrates a graph including results of a drop test over time;

FIG. 19 illustrates a graph of measured impact force as impact energy is increased;

FIG. 20 illustrates a discrete impact control and measurement process; and

FIG. 21 illustrates a warning process; and

FIG. 22 illustrates a basic force sensor system for controlled insertion;

FIG. 23 illustrates an FR curve including TmIF and mIF as functions of displacement;

FIG. 24 illustrates a generic force sensor tool to access variables of interest in FIG. 23;

FIG. 25 illustrates a B-cloud tracking process using TmIF and MIF measurements;

FIG. 26 illustrates a control system for the "controlled action" referenced in FIG. 25;

FIG. 27 illustrates possible B-cloud regulation strategies; and

DETAILED DESCRIPTION OF THE INVENTION

Figure 1:
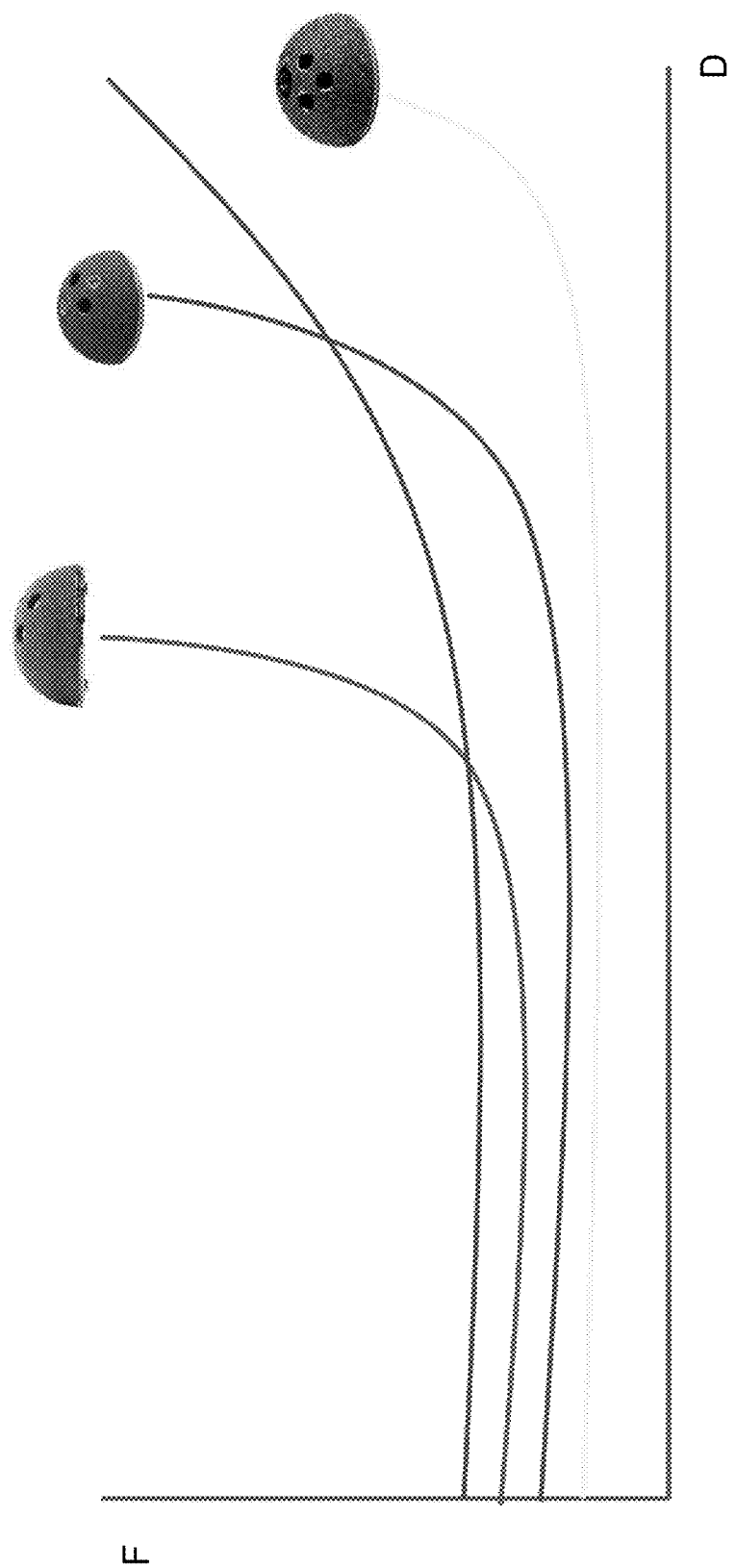
FIG. 1 illustrates a set of "cup prints" for a number of interactions between a cup and a cavity.

Embodiments of the present invention provide a system and method for allowing any surgeon, including those surgeons who perform a fewer number of a replacement procedure as compared to a more experienced surgeon who performs a greater number of procedures, to provide an improved likelihood of a favorable outcome approaching, if not exceeding, a likelihood of a favorable outcome as performed by a very experienced surgeon with the replacement procedure, such as by understanding the prosthesis installation environment (e.g., cup/cavity interface) and to provide intelligent and interactive tools and methods to standardize the installation process. The following description is presented to enable one of ordinary skill in the art to make and use the invention and is provided in the context of a patent application and its requirements.

Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Definitions

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The following definitions apply to some of the aspects described with respect to some embodiments of the invention. These definitions may likewise be expanded upon herein.

As used herein, the term "or" includes "and/or" and the term "and/or" includes any and all combinations of one or more of the associated listed items. Expressions such as "at least one of," when preceding a list of elements, modify the entire list of elements and do not modify the individual elements of the list.

As used herein, the singular terms "a," "an," and "the" include plural referents unless the context clearly dictates otherwise. Thus, for example, reference to an object can include multiple objects unless the context clearly dictates otherwise.

Also, as used in the description herein and throughout the claims that follow, the meaning of "in" includes "in" and "on" unless the context clearly dictates otherwise. It will be understood that when an element is referred to as being "on" another element, it can be directly on the other element or intervening elements may be present therebetween. In contrast, when an element is referred to as being "directly on" another element, there are no intervening elements present.

As used herein, the term "set" refers to a collection of one or more objects. Thus, for example, a set of objects can include a single object or multiple objects. Objects of a set also can be referred to as members of the set. Objects of a set can be the same or different. In some instances, objects of a set can share one or more common properties.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "connect," "connected," and "connecting" refer to a direct attachment or link. Connected objects have no or no substantial intermediary object or set of objects, as the context indicates.

As used herein, the terms "couple," "coupled," and "coupling" refer to an operational connection or linking. Coupled objects can be directly connected to one another or can be indirectly connected to one another, such as via an intermediary set of objects.

As used herein, the terms "substantially" and "substantial" refer to a considerable degree or extent. When used in conjunction with an event or circumstance, the terms can refer to instances in which the event or circumstance occurs precisely as well as instances in which the event or circumstance occurs to a close approximation, such as accounting for typical tolerance levels or variability of the embodiments described herein.

As used herein, the terms "optional" and "optionally" mean that the subsequently described event or circumstance may or may not occur and that the description includes instances where the event or circumstance occurs and instances in which it does not.

As used herein, the term "bone" means rigid connective tissue that constitute part of a vertebral skeleton, including mineralized osseous tissue, particularly in the context of a living patient undergoing a prosthesis implant into a portion of cortical bone. A living patient, and a surgeon for the patient, both have significant interests in reducing attendant risks of conventional implanting techniques including fracturing/shattering the bone and improper installation and positioning of the prosthesis within the framework of the patient's skeletal system and operation.

As used herein, the term "size" refers to a characteristic dimension of an object. Thus, for example, a size of an object that is spherical can refer to a diameter of the object. In the case of an object that is non-spherical, a size of the non-spherical object can refer to a diameter of a corresponding spherical object, where the corresponding spherical object exhibits or has a particular set of derivable or measurable properties that are substantially the same as those of the non-spherical object. Thus, for example, a size of a non-spherical object can refer to a diameter of a corresponding spherical object that exhibits light scattering or other properties that are substantially the same as those of the non-spherical object. Alternatively, or in conjunction, a size of a non-spherical object can refer to an average of various orthogonal dimensions of the object. Thus, for example, a size of an object that is a spheroidal can refer to an average of a major axis and a minor axis of the object. When referring to a set of objects as having a particular size, it is contemplated that the objects can have a distribution of sizes around the particular size. Thus, as used herein, a size of a set of objects can refer to a typical size of a distribution of sizes, such as an average size, a median size, or a peak size.

As used herein, mallet or hammer refers to an orthopedic device made of stainless steel or other dense material having a weight generally a carpenter's hammer and a stonemason's lump hammer.

As used herein, an impact force for impacting an acetabular component (e.g., an acetabular cup prosthesis) includes forces from striking an impact rod multiple times with the orthopedic device that are generally similar to the forces that may be used to drive a three inch nail into a piece of lumber using the carpenter's hammer by striking the nail approximately a half-dozen times to completely seat the nail. Without limiting the preceding definition, a representative value in some instances includes a force of approximately 10 lbs./square inch.

As used herein, the term "real-time" sensing means sensing relevant parameters (e.g., force, acceleration, vibration, acoustic, and the like) during processing.

The following description relates to improvements in a wide range of prostheses installations into live bones of patients of surgeons. The following discussion focuses primarily on total hip replacement (THR) in which an acetabular cup prosthesis is installed into the pelvis of the patient. This cup is complementary to a ball and stem (i.e., a femoral prosthesis) installed into an end of a femur engaging the acetabulum undergoing repair.

Embodiments of the present invention may include one of more solutions to the above problems. The incorporated U.S. Pat. No. 9,168,154 includes a description of several embodiments, sometimes referred to herein as a BMD3 device, some of which illustrate a principle for breaking down large forces associated with the discrete blows of a mallet into a series of small taps, which in turn perform similarly in a stepwise fashion while being more efficient and safer. The BMD3 device produces the same displacement of the implant without the need for the large forces from the repeated impacts from the mallet. The BMD3 device may allow modulation of force required for cup insertion based on bone density, cup geometry, and surface roughness. Further, a use of the BMD3 device may result in the acetabulum experiencing less stress and deformation and the implant may experience a significantly smoother sinking pattern into the acetabulum during installation. Some embodiments of the BMD3 device may provide a superior approach to these problems, however, described herein are two problems that can be approached separately and with more basic methods as an alternative to, or in addition to, a BMD3 device. An issue of undesirable torques and moment arms is primarily related to the primitive method currently used by surgeons, which involves manually banging the mallet on the impaction plate. The amount of force utilized in this process is also non-standardized and somewhat out of control.

With respect to the impaction plate and undesirable torques, an embodiment of the present invention may include a simple mechanical solution as an alternative to some BMD3 devices, which can be utilized by the surgeon's hand or by a robotic machine. A direction of the impact may be directed or focused by any number of standard techniques (e.g., A-frame, C-arm or navigation system). Elsewhere described herein is a refinement of this process by considering directionality in the reaming process, in contrast to only considering it just prior to impaction. First, we propose to eliminate the undesirable torques by delivering the impacts by a sledgehammer device (or a hollow cylindrical mass) that travels over a stainless rod.

As noted in the background, the surgeon prepares the surface of the hipbone which includes attachment of the acetabular prosthesis to the pelvis. Conventionally, this attachment includes a manual implantation in which a mallet is used to strike a tamp that contacts some part of the acetabular prosthesis. Repeatedly striking the tamp drives the acetabular prosthesis into the acetabulum. Irrespective of whether current tools of computer navigation, fluoroscopy, robotics (and other intra-operative measuring tools) have been used, it is extremely unlikely that the acetabular prosthesis will be in the correct orientation once it has been seated to the proper depth by the series of hammer strikes. After manual implantation in this way, the surgeon then may apply a series of adjusting strikes around a perimeter of the acetabular prosthesis to attempt to adjust to the desired orientation. Currently such post-impaction result is accepted as many surgeons believe that post-impaction adjustment creates an unpredictable and unreliable change which does not therefore warrant any attempts for post-impaction adjustment.

In most cases, any and all surgeons including an inexperienced surgeon may not be able to achieve the desired orientation of the acetabular prosthesis in the pelvis by conventional solutions due to unpredictability of the orientation changes responsive to these adjusting strikes. As noted above, it is most common for any surgeon to avoid post-impaction adjustment as most surgeons understand that they do not have a reliable system or method for improving any particular orientation and could easily introduce more/greater error. The computer navigation systems, fluoroscopy, and other measuring tools are able to provide the surgeon with information about the current orientation of the prosthesis during an operation and after the prosthesis has been installed and its deviation from the desired orientation, but the navigation systems (and others) do not protect against torsional forces created by the implanting/positioning strikes. The prosthesis will find its own position in the acetabulum based on the axial and torsional forces created by the blows of the mallet. Even those navigation systems used with robotic systems (e.g., MAKE) that attempt to secure an implant in the desired orientation prior to impaction are not guaranteed to result in the installation of the implant at the desired orientation because the actual implanting forces are applied by a surgeon swinging a mallet to manually strike the tamp.

A Behzadi Medical Device (BMD) is herein described and enabled that eliminates this crude method (i.e., mallet, tamp, and surgeon-applied mechanical implanting force) of the prosthesis (e.g., the acetabular cup). A surgeon using the BMD is able to insert the prosthesis exactly where desired with proper force, finesse, and accuracy. Depending upon implementation details, the installation includes insertion of the prosthesis into patient bone, within a desired threshold of metrics for insertion depth and location) and may also include, when appropriate and/or desired, positioning at a desired orientation with the desired threshold further including metrics for insertion orientation). The use of the BMD reduces risks of fracturing and/or shattering the bone receiving the prosthesis and allows for rapid, efficient, and accurate (atraumatic) installation of the prosthesis. The BMD provides a viable interface for computer navigation assistance (also useable with all intraoperative measuring tools including fluoroscopy) during the installation as a lighter more responsive touch may be used.

The BMD encompasses many different embodiments for installation and/or positioning of a prosthesis and may be adapted for a wide range of prostheses in addition to installation and/or positioning of an acetabular prosthesis during THR.

FIG. 1-FIG. 6 illustrate a set of graphs of Force (y-axis) versus distance (x-axis). FIG. 1 illustrates a set of "cup prints" for a number of interactions between a cup and a cavity. Each combination of an implant (e.g., an acetabular cup) and its implant site (e.g., a reamed cavity in an acetabulum) has a resistive force (FR) that may be thought of as a particular cup print unique for that combination. FIG. 1 includes four such cup prints. Factors influencing the cup print include bone density (hard/soft), cup geometry (elliptical/spherical), cup surface preparation (e.g., roughness), and reaming preparation. Other sensors or sets of sensors may produce a more complex characteristic sensor print for processing of a prosthesis or portion of a prosthesis.

Figure 2:
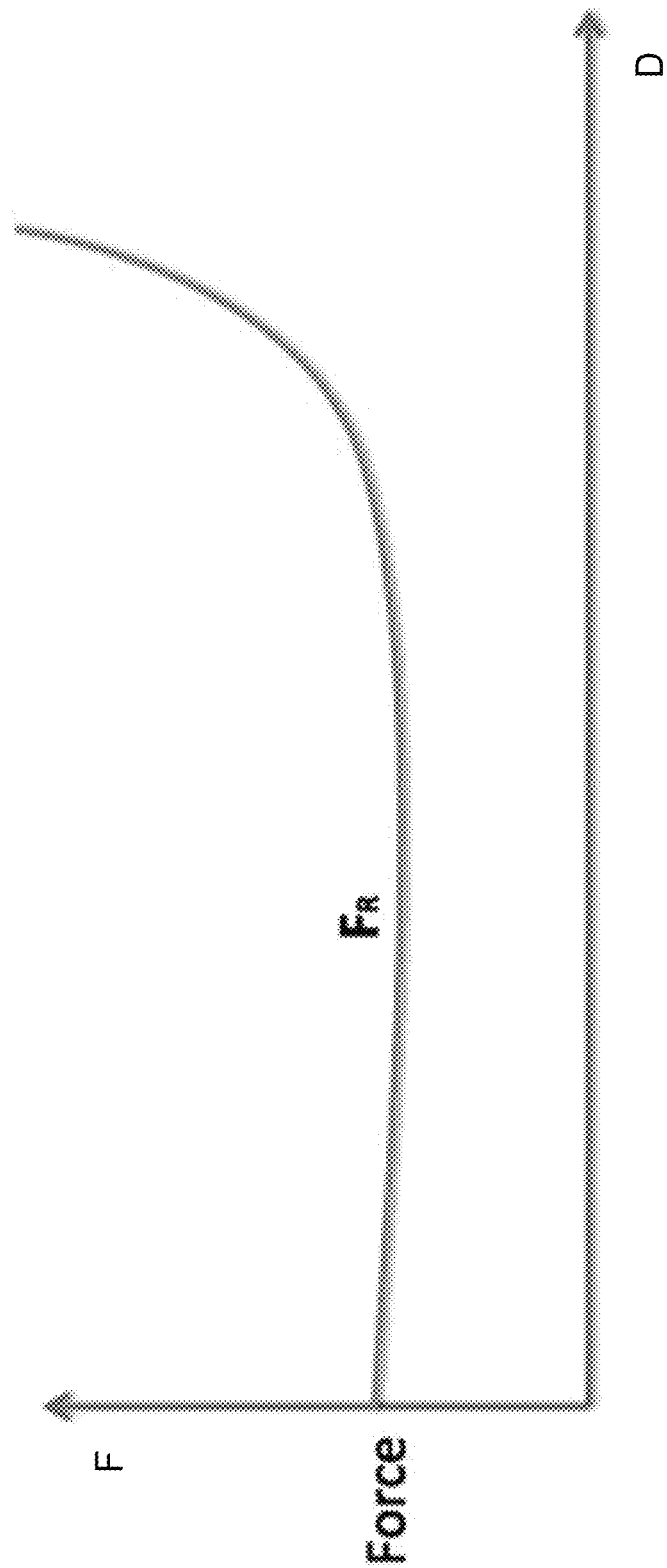
FIG. 2 illustrates a particular one representative cup print.
Figure 3:
FIG. 3 illustrates a controlled modulated installation force envelope.

FIG. 2 illustrates a particular one representative cup print that relates to one cup/cavity interaction. FIG. 3 illustrates a controlled modulated installation force envelope superimposed over the cup print of FIG. 2. Typically, the amplitude of the modulation increases as the implant is seated, with too great of force increasing a risk of fracture and tool little force increasing a risk of poor "seatedness"—a property of the implant relating to how well seated it is within its installation site.

Figure 4:
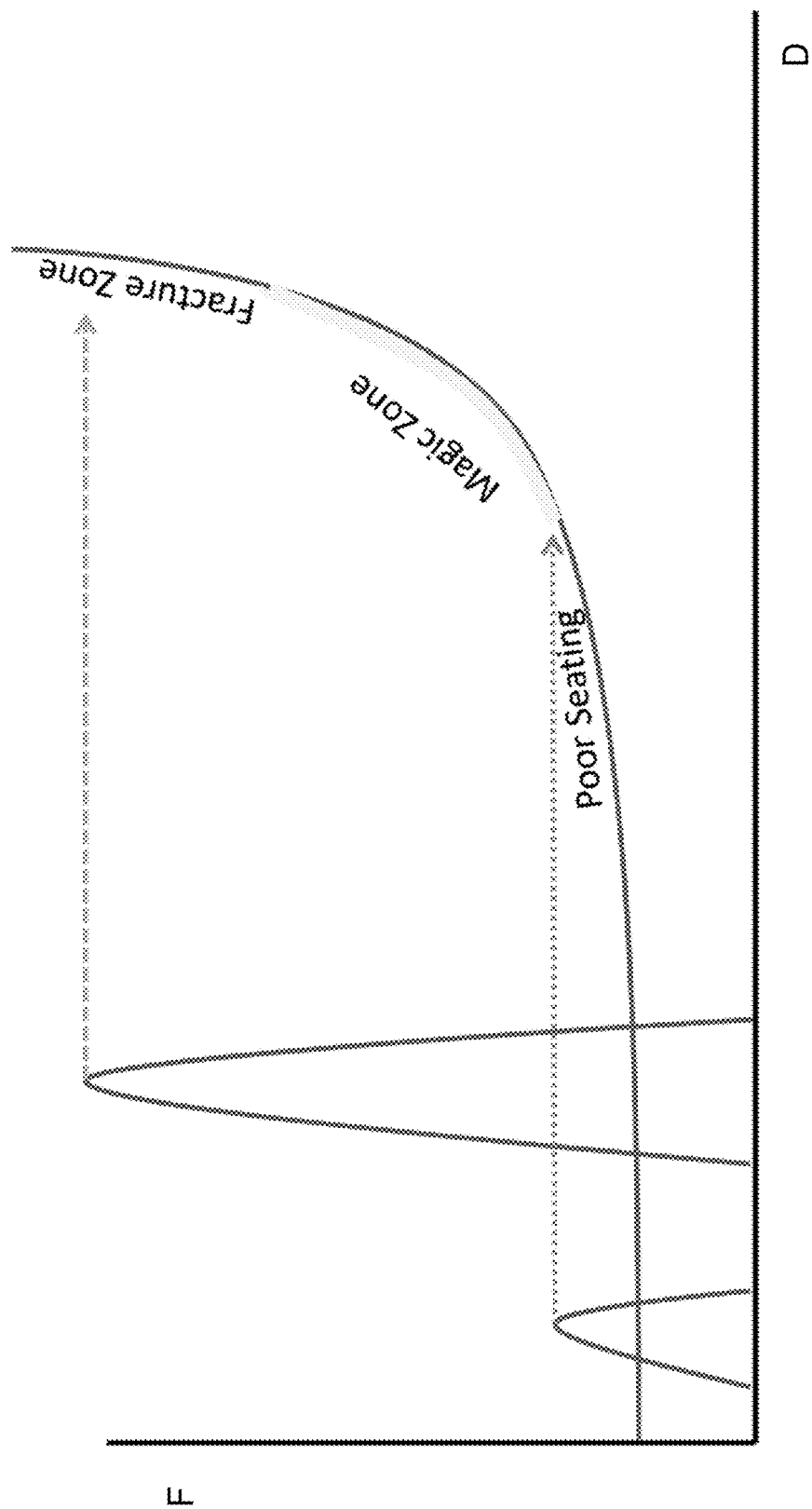
FIG. 4 illustrates an example installation force envelope that is representative of use of a mallet in its production.

FIG. 4 illustrates an example installation force envelope that is representative of use of a mallet in its production. In this example, a surgeon "feels" and "listens" for the magic zone—adequate insertion and good pull-out force (seatedness) while being concerned with every strike that the installation site may fracture. The non-controlled mallet-applied installation force is shown superimposed over the cup print of FIG. 2.

Figure 5:
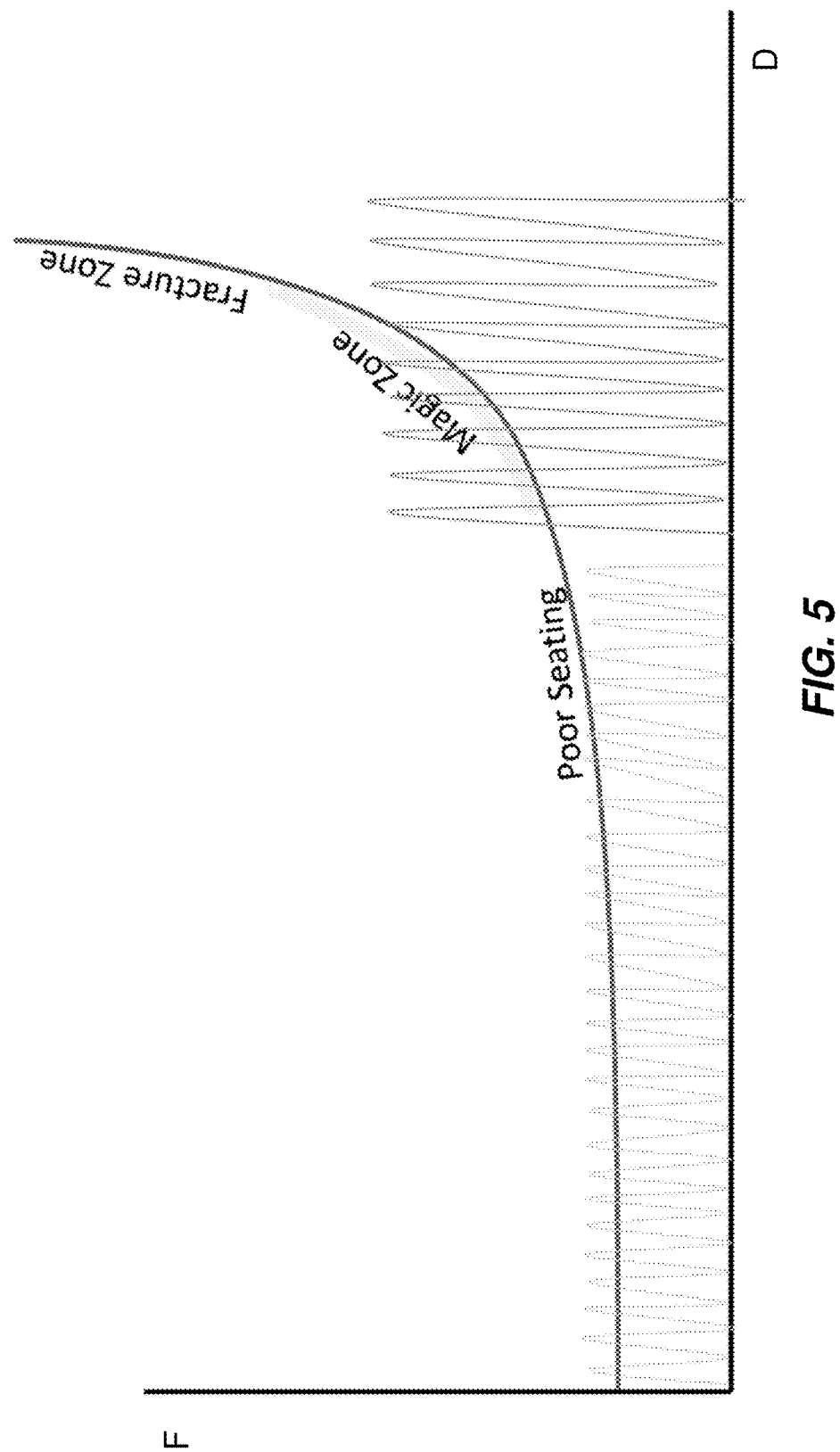
FIG. 5 illustrates an example installation force envelope that is representative of use of a BMD3 in its production.

FIG. 5 illustrates an example installation force envelope that is representative of use of a BMD3 in its production. In this example, a surgeon dials into the magic zone by gradually changing the BMD3 force-applied profile. A BMD3 controlled modulated installation force envelope is shown superimposed over the cup print of FIG. 2. The surgeon is able to use a BMD3-type tool to walk the envelope (the contour of the installation force envelope) up and into the magic zone with greatly improved confidence of achieving the desired seatedness without greatly increasing a risk of fracture. Frictional forces may be decreased (effectively and realistically) at certain frequencies that may improve as the frequency increases (e.g., one to hundreds of Hertz or more, one-two kilohertz or more, and beyond to ultrasonic frequencies above two kilohertz). The reduced frictional forces may also enable easier alignment of the cup during and/or after insertion/placement.

Figure 6:
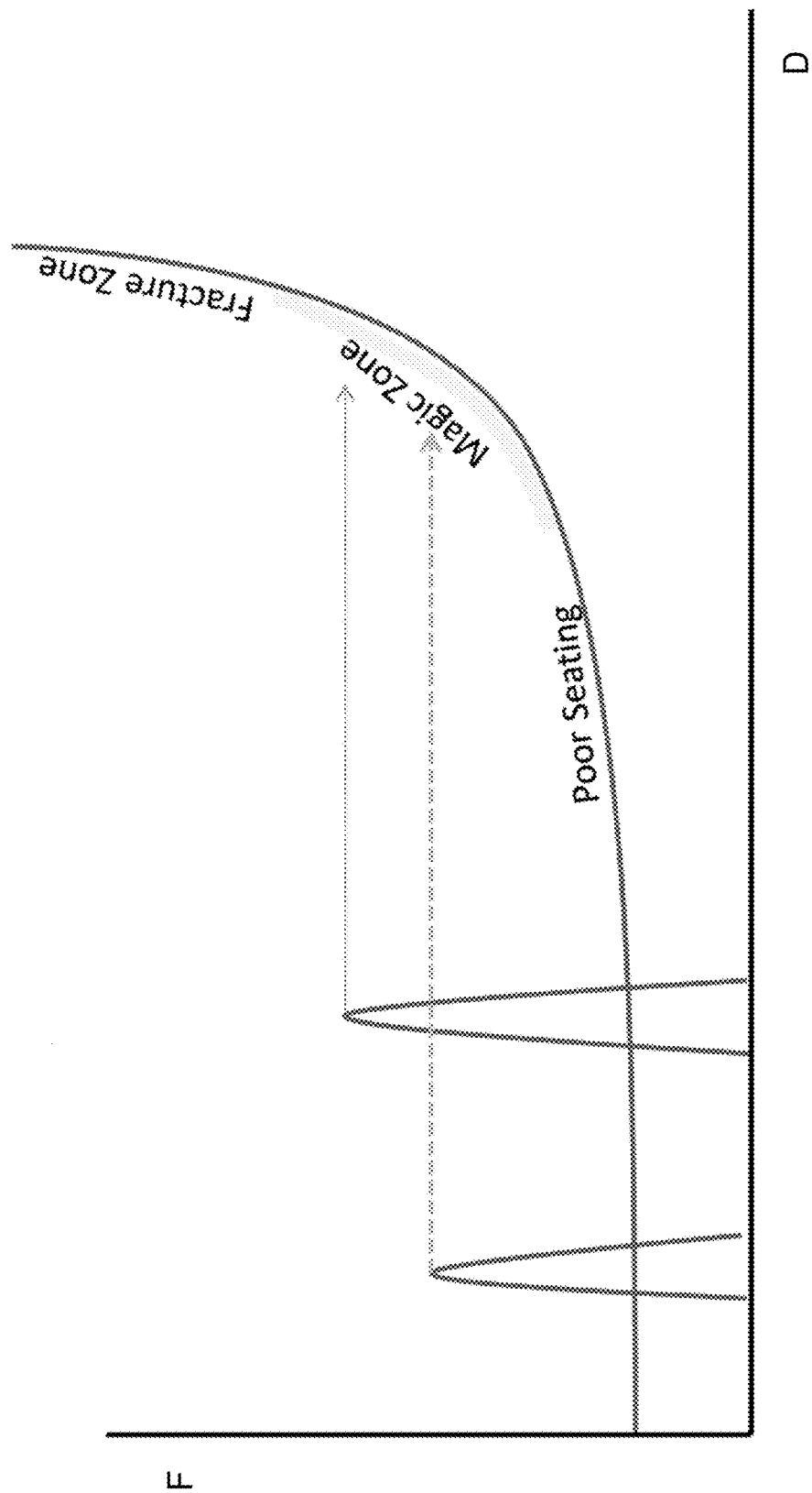
FIG. 6 illustrates an example installation force envelope that is representative of use of a BMD4 in its production.

FIG. 6 illustrates an example installation force envelope that is representative of use of a BMD4 in its production. In this example, a surgeon dials into the magic zone by dialing the BMD4 force-applied profile. A BMD4 controlled modulated installation force envelope is shown superimposed over the cup print of FIG. 2. The surgeon is able to use a BMD4-type tool to dial into the magic zone (the contour of the installation force envelope) with greatly improved confidence of achieving the desired seatedness without greatly increasing a risk of fracture and while maintaining a desired alignment/positioning, for example, within the Lewinski range.

A hybrid BMD3/BMD4 embodiment may provide a hybrid controlled modulated installation force envelope that offers advantages of both BMD3 and BMD4.

Figure 7:
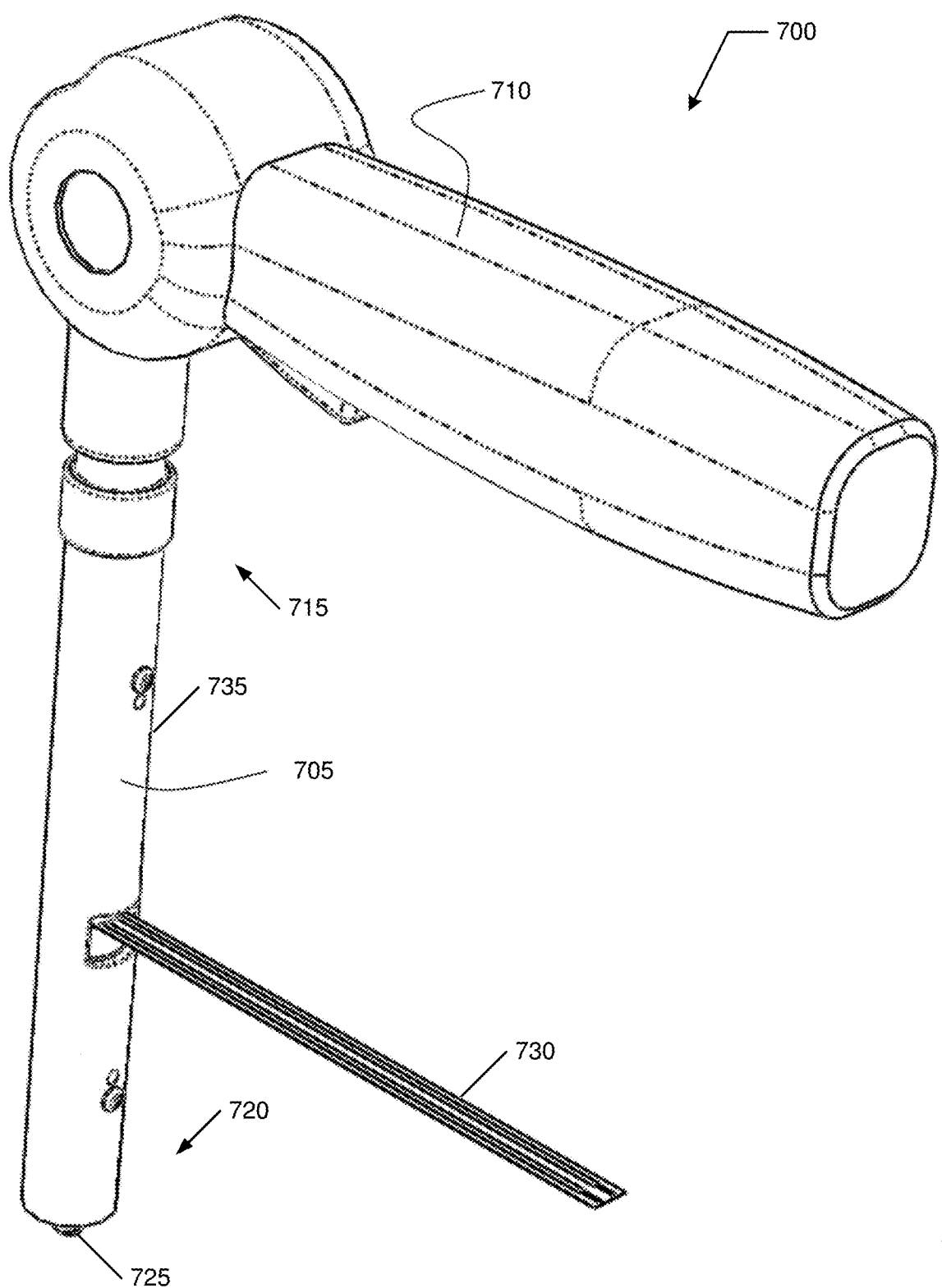
FIG. 7-FIG. 10 relate to a vibratory Behzadi Medical Device (BMD3)

FIG. 7 illustrates a representative installation gun. The installation gun may be operable with operable using pneumatics, though other implementations may use other mechanisms including motors for creating a desired vibratory motion of prosthesis to be installed.

The installation gun may be used to control precisely one or both of (i) insertion, and (ii) abduction and anteversion angles of a prosthetic component. Installation gun 100 preferably allows both installation of an acetabular cup into an acetabulum at a desired depth and orientation of the cup for both abduction and anteversion to desired values.

The installation gun may include a controller with a handle supporting an elongate tube that terminates in an adapter that engages a cup. Operation of a trigger may initiate a motion of the elongate tube. This motion is referred to herein as an installation force and/or installation motion that is much less than the impact force used in a conventional replacement process. An exterior housing allows the operator to hold and position the prosthesis (e.g., the cup) while elongate tube moves within. Some embodiments may include a handle or other grip in addition to or in lieu of the housing that allows the operator to hold and operate installation gun without interfering with the mechanism that provides a direct transfer of installation motion to the prosthesis. The illustrated embodiment may include the prosthesis held securely by adapter allowing a tilting and/or rotation of gun about any axis to be reflected in the position/orientation of the secured prosthesis.

The installation motion includes constant, cyclic, periodic, and/or random motion (amplitude and/or frequency) that allows the operator to install the cup into the desired position (depth and orientation) without application of an impact force. There may be continuous movement or oscillations in one or more of six degrees of freedom including translation(s) and/or rotation(s) of adapter 146 about the X, Y, Z axes (e.g., oscillating translation(s) and/or oscillating/continuous rotation(s) which could be different for different axes such as translating back and forth in the direction of the longitudinal axis of the central support while rotating continuously around the longitudinal axis). This installation motion may include continuous or intermittent very high frequency movements and oscillations of small amplitude that allow the operator to easily install the prosthetic component in the desired location, and preferably also to allow the operator to also set the desired angles for abduction and anteversion.

In some implementations, the controller includes a stored program processing system that includes a processing unit that executes instructions retrieved from memory. Those instructions could control the selection of the motion parameters autonomously to achieve desired values for depth, abduction and anteversion entered into by the surgeon or by a computer aided medical computing system such as the computer navigation system. Alternatively, those instructions could be used to supplement manual operation to aid or suggest selection of the motion parameters.

For more automated systems, consistent and unvarying motion parameters are not required, and it may be that a varying dynamic adjustment of the motion parameters better conform to an adjustment profile of the cup installed into the acetabulum and status of the installation. An adjustment profile is a characterization of the relative ease by which depth, abduction and anteversion angles may be adjusted in positive and negative directions. In some situations, these values may not be the same and the installation gun could be enhanced to adjust for these differences. For example, a unit of force applied to pure positive anteversion may adjust anteversion in the positive direction by a first unit of distance while under the same conditions that unit of force applied to pure negative anteversion may adjust anteversion in the negative direction by a second unit of distance different from the first unit. And these differences may vary as a function of the magnitude of the actual angle(s). For example, as the anteversion increases it may be that the same unit of force results in a different responsive change in the actual distance adjusted. The adjustment profile when used helps the operator when selecting the actuators and the impact force(s) to be applied. Using a feedback system of the current real-time depth and orientation enables the adjustment profile to dynamically select/modify the motion parameters appropriately during different phases of the installation. One set of motion parameters may be used when primarily setting the depth of the implant and then another set used when the desired depth is achieved so that fine tuning of the abduction and anteversion angles is accomplished more efficiently, all without use of impact forces in setting the depth and/or angle adjustment(s).

This device better enables computer navigation as the installation/adjustment forces are reduced as compared to the impacting method. This makes the required forces more compatible with computer navigation systems used in medical procedures which do not have the capabilities or control systems in place to actually provide impacting forces for seating the prosthetic component. And without that, the computer is at best relegated to a role of providing after-the-fact assessments of the consequences of the surgeon's manual strikes of the orthopedic mallet. (Also provides information before and during the impaction. It is a problem that the very act of impaction introduces variability and error in positioning and alignment of the prosthesis.

Figure 8:
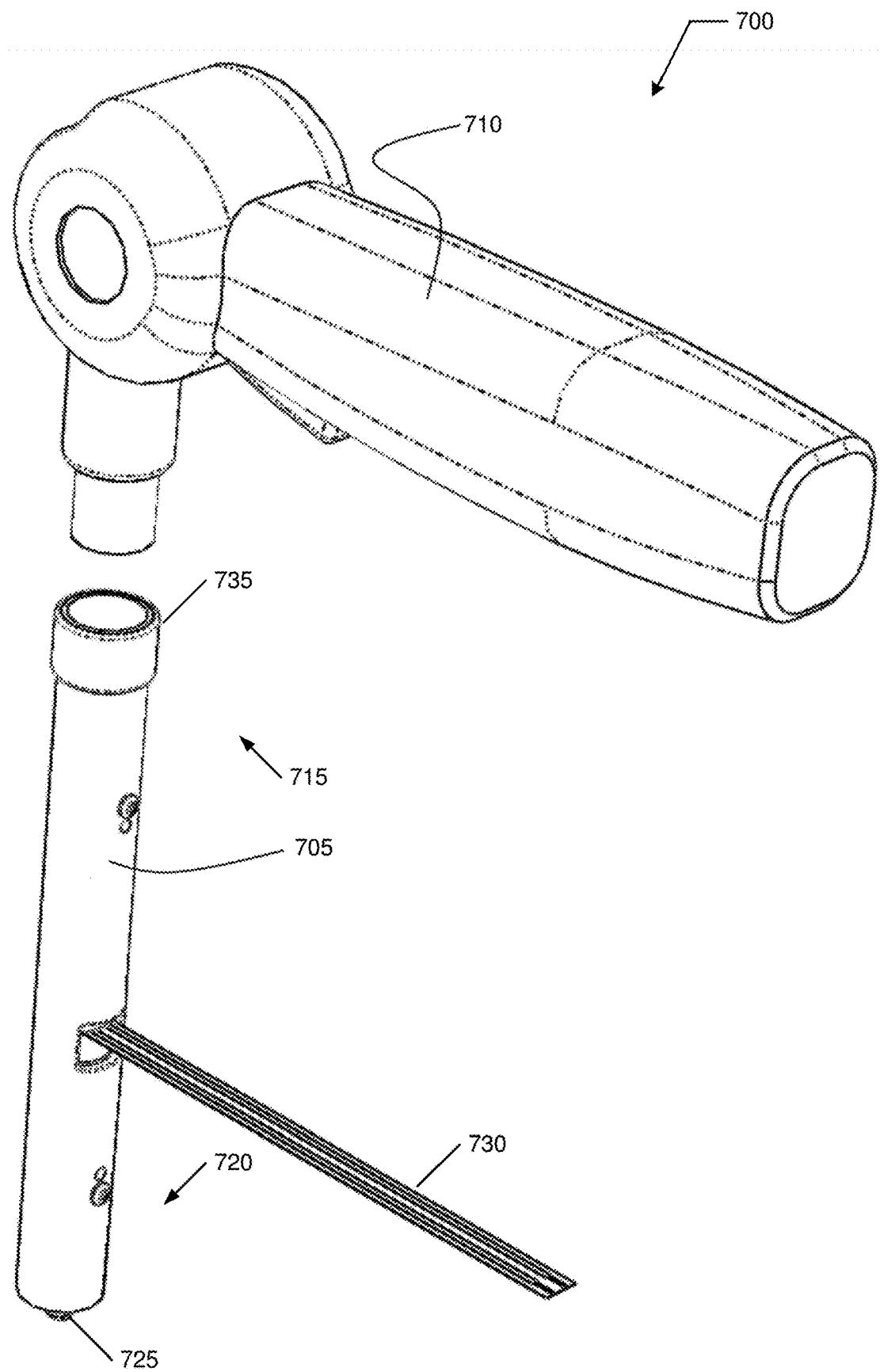
Figure 9:
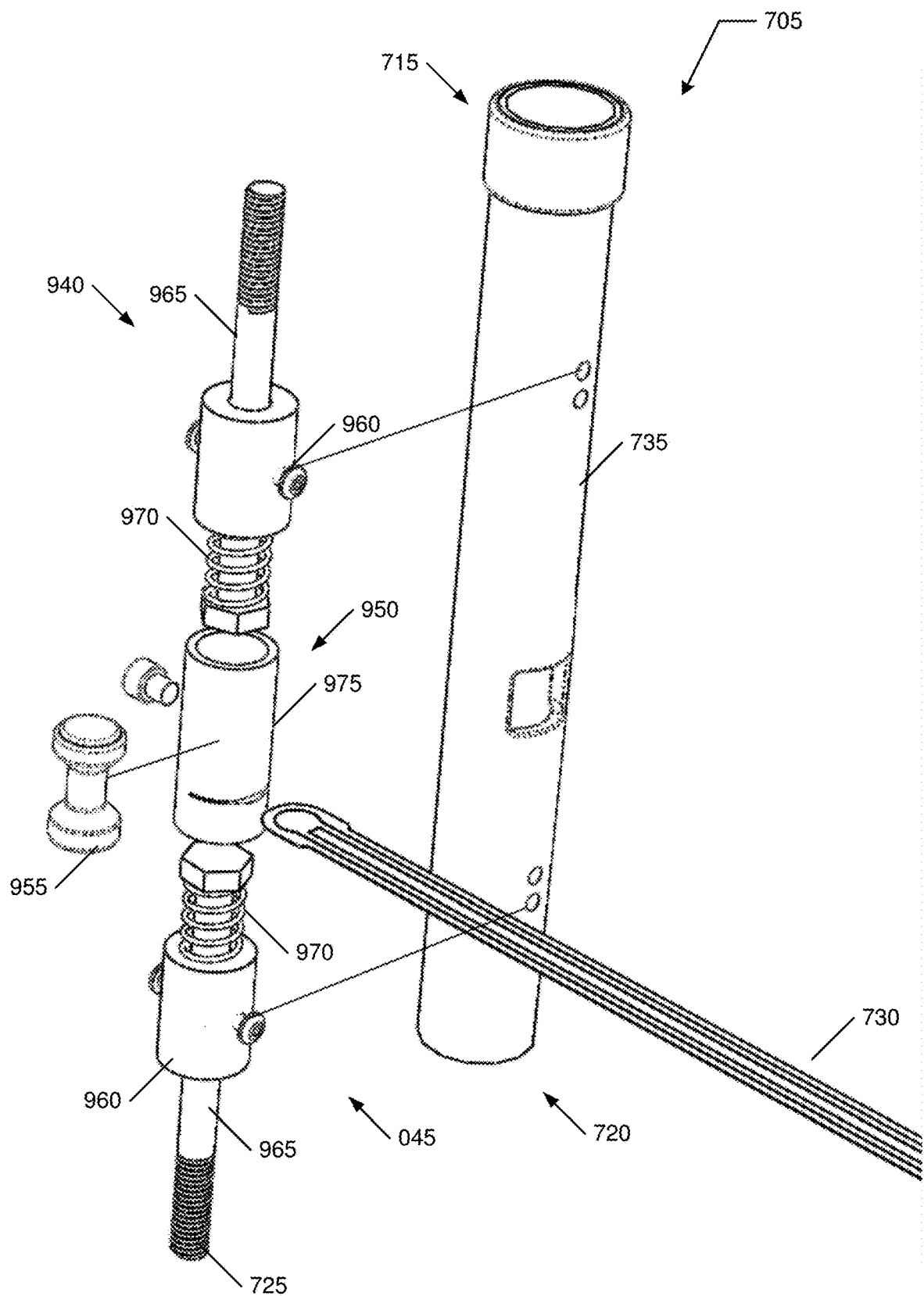
Figure 10:
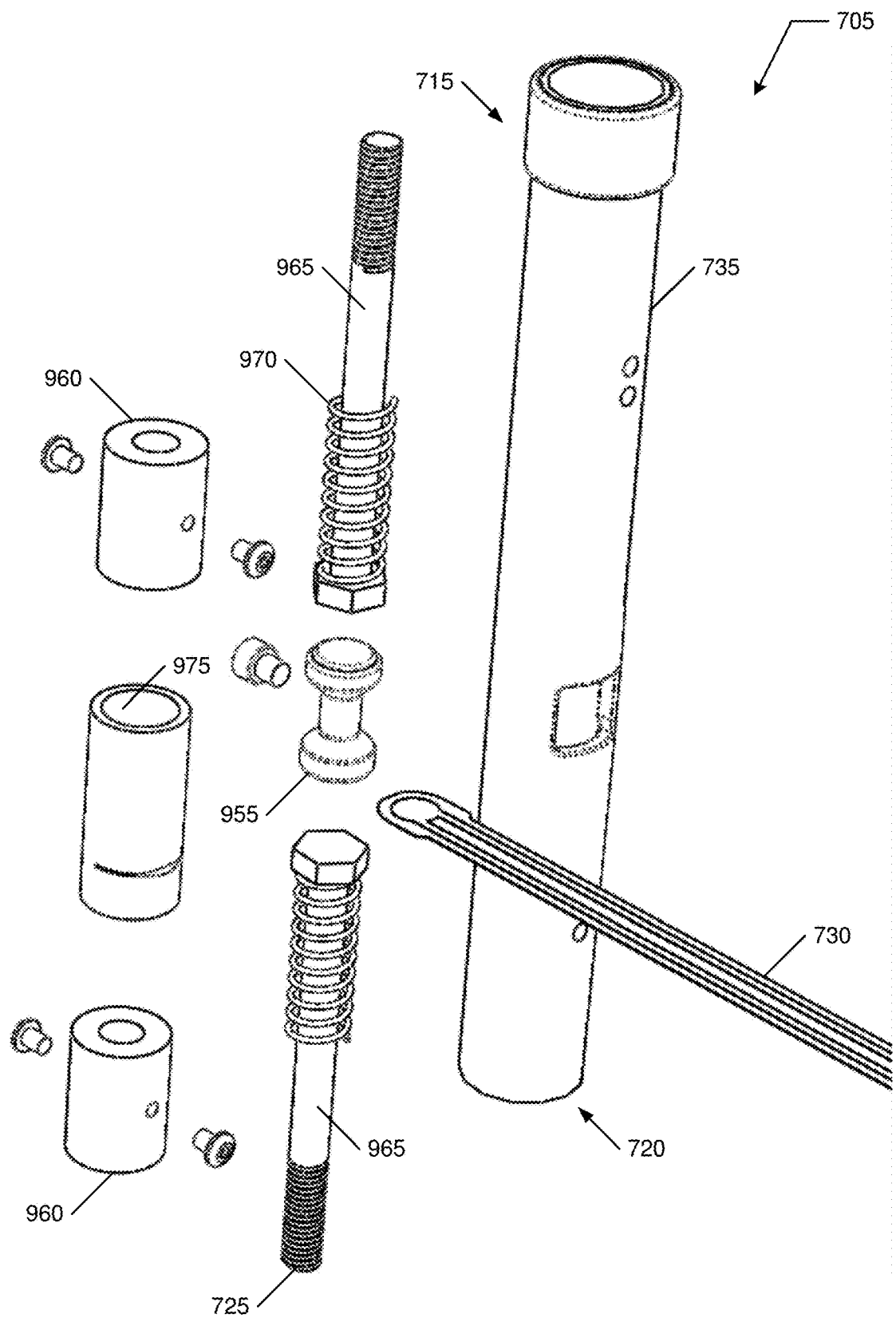
Figure 11:
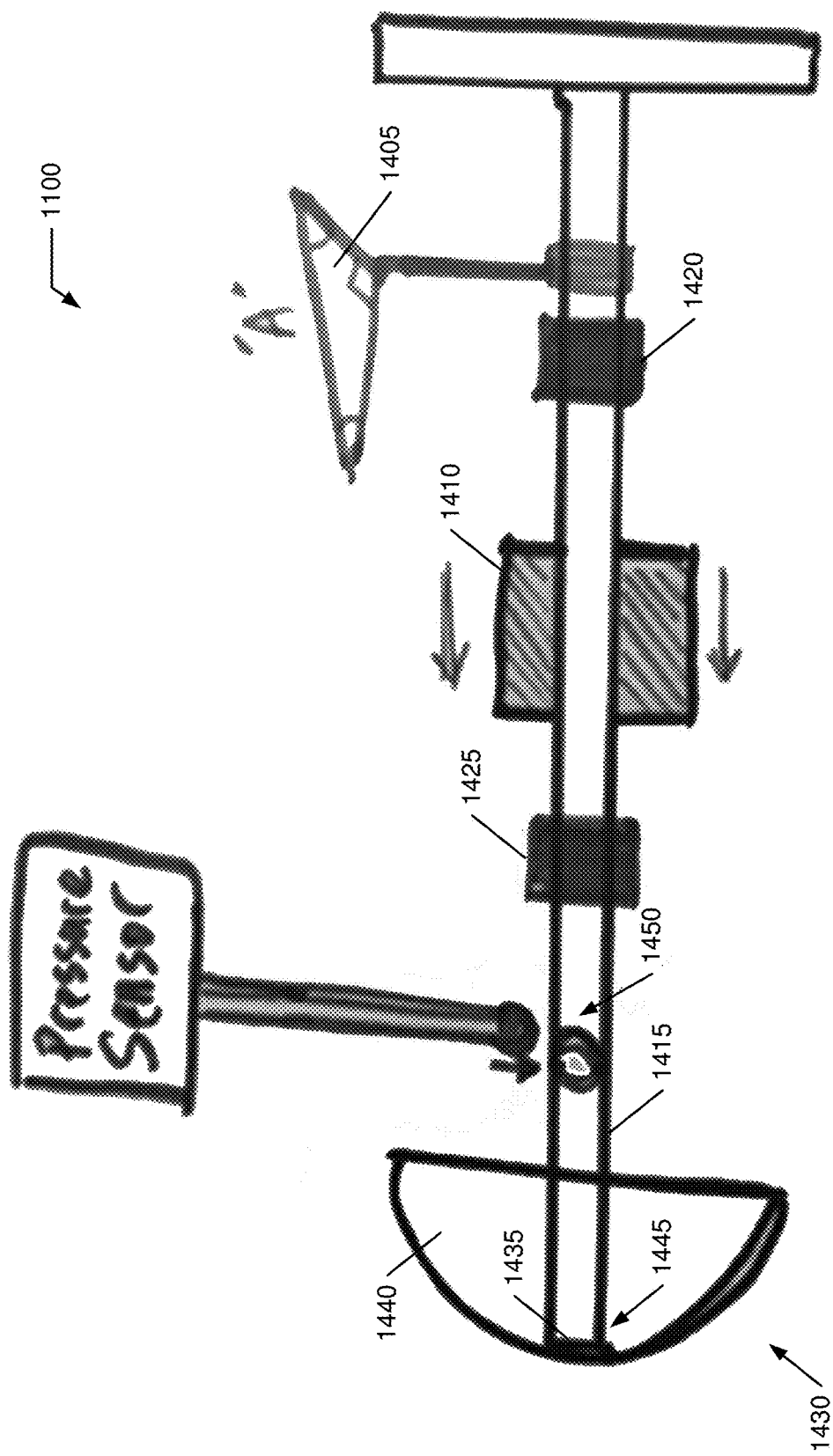
FIG. 11 illustrates an embodiment for a sliding impact device having a pressure sensor to provide feedback and attachment of an optional navigation device.

FIG. 7 illustrates a representative installation system 700 including a pulse transfer assembly 705 and an oscillation engine 710; FIG. 8 illustrates a disassembly of second representative installation system 700; FIG. 9 illustrates a first disassembly view of pulse transfer assembly 705; and FIG. 10 illustrates a second disassembly view of pulse transfer assembly 705 of installation system 700.

Installation system 700 is designed for installing a prosthesis that, in turn, is configured to be implanted into a portion of bone at a desired implantation depth. The prosthesis includes some type of attachment system (e.g., one or more threaded inserts, mechanical coupler, link, or the like) allowing the prosthesis to be securely and rigidly held by an object such that a translation and/or a rotation of the object about any axis results in a direct corresponding translation and/or rotation of the secured prosthesis.

Oscillation engine 710 includes a controller coupled to a vibratory machine that generates an original series of pulses having a generation pattern. This generation pattern defines a first duty cycle of the original series of pulses including one or more of a first pulse amplitude, a first pulse direction, a first pulse duration, and a first pulse time window. This is not to suggest that the amplitude, direction, duration, or pulse time window for each pulse of the original pulse series are uniform with respect to each other. Pulse direction may include motion having any of six degrees of freedom—translation along one or more axes of any axis of three orthogonal axes and/or rotation about one or more of these three axes. Oscillation engine 710 includes an electric motor powered by energy from a battery, though other motors and energy sources may be used.

Pulse transfer assembly 705 includes a proximal end 715 coupled to oscillation engine 710 and a distal end 720, spaced from proximal end 720, coupled to the prosthesis using a connector system 725. Pulse transfer assembly 705 receives the original series of pulses from oscillation engine 710 and produces, responsive to the original series of pulses, an installation series of pulses having an installation pattern. Similar to the generation pattern, the installation pattern defines a second duty cycle of the installation series of pulses including a second pulse amplitude, a second pulse direction, a second pulse duration, and a second pulse time window. Again, this is not to suggest that the amplitude, direction, duration, or pulse time window for each pulse of the installation pulse series are uniform with respect to each other, nor does it imply that they are non-uniform. Pulse direction may include motion having any of six degrees of freedom—translation along one or more of any axes of three orthogonal axes and/or rotation about one or more of these three axes.

For some embodiments of pulse transfer assembly 705, the installation series of pulses will be strongly linked to the original series and there will be a close match, if not identical match, between the two series. Some embodiments may include a more complex pulse transfer assembly 705 that produces an installation series that is more different, or very different, from the original series.

Connector system 725 (e.g., one or more threaded studs complementary to the threaded inserts of the prosthesis, or other complementary mechanical coupling system) is disposed at proximal end 720. Connector system 725 is configured to secure and rigidly hold the prosthesis. In this way, the attached prosthesis becomes a secured prosthesis when engaged with connector system 725.

Pulse transfer assembly 705 communicates the installation series of pulses to the secured prosthesis and produces an applied series of pulses that are responsive to the installation series of pulses. Similar to the generation pattern and the installation pattern, the applied pattern defines a third duty cycle of the applied series of pulses including a third pulse amplitude, a third pulse direction, a third pulse duration, and a third pulse time window. Again, this is not to suggest that the amplitude, direction, duration, or pulse time window for each pulse of the applied pulse series are uniform with respect to each other. Pulse direction may include motion having any of six degrees of freedom—translation along one or more of any axes of three orthogonal axes and/or rotation about one or more of these three axes.

For some embodiments of pulse transfer assembly 705, the applied series of pulses will be strongly linked to the original series and/or the installation series and there will be a close, if not identical, match between the series. Some embodiments may include a more complex pulse transfer assembly 705 that produces an applied series that is more different, or very different, from the original series and/or the installation series. In some embodiments, for example one or more components may be integrated together (for example, integrating oscillation engine 710 with pulse transfer assembly 705) so that the first series and the second series, if they exist independently are nearly identical if not identical).

The applied series of pulses are designed to impart a vibratory motion to the secured prosthesis that enable an installation of the secured prosthesis into the portion of bone to within 95% of the desired implantation depth without a manual impact. That is, in operation, the original pulses from oscillation engine 710 propagate through pulse transfer assembly 705 (with implementation-depending varying levels of fidelity) to produce the vibratory motion to the prosthesis secured to connector system 725. In a first implementation, the vibratory motion allows implanting without manual impacts on the prosthesis and in a second mode an orientation of the implanted secured prosthesis may be adjusted by rotations of installation system 700 while the vibratory motion is active, also without manual impact. In some implementations, the pulse generation may produce different vibratory motions optimized for these different modes.

Installation system 700 includes an optional sensor 730 (e.g., a flex sensor or the like) to provide a measurement (e.g., quantitative and/or qualitative) of the installation pulse pattern communicated by pulse transfer assembly 705. This measurement may be used as part of a manual or computerized feedback system to aid in installation of a prosthesis. For example, in some implementations, the desired applied pulse pattern of the applied series of pulses (e.g., the vibrational motion of the prosthesis) may be a function of a particular installation pulse pattern, which can be measured and set through sensor 730. In addition to, or alternatively, other sensors may aid the surgeon or an automated installation system operating installation system 700, such as a bone density sensor or other mechanism to characterize the bone receiving the prosthesis to establish a desired applied pulse pattern for optimal installation. In some implementations, sensor 730 measures force magnitude as part of the installation pulse pattern.

The disassembled views of FIG. 9 and FIG. 10 detail a particular implementation of pulse transfer assembly 705, it being understood that there are many possible ways of creating and communicating an applied pulse pattern responsive to a series of generation pulses from an oscillation engine. The illustrated structure of FIG. 9 and FIG. 10 generate primarily longitudinal/axial pulses in response to primarily longitudinal/axial generation pulses from oscillation engine 710.

Pulse transfer assembly 705 includes an outer housing 735 containing an upper transfer assembly 940, a lower transfer assembly 945 and a central assembly 950. Central assembly 950 includes a double anvil 955 that couples upper transfer assembly 940 to lower transfer assembly 945. Outer housing 935 and central assembly 950 each include a port allowing sensor 930 to be inserted into central assembly 950 between an end of double anvil 955 and one of the upper/lower transfer assemblies.

Upper transfer assembly 940 and lower transfer assembly 945 each include a support 960 coupled to outer housing 735 by a pair of connectors. A transfer rod 965 is moveably disposed through an axial aperture in each support 960, with each transfer rod 965 including a head at one end configured to strike an end of double anvil 955 and a coupling structure at a second end. A compression spring 970 is disposed on each transfer rod 965 between support 960 and the head. The coupling structure of upper transfer assembly 940 cooperates with oscillation engine 710 to receive the generated pulse series. The coupling structure of lower transfer assembly 945 includes connector system 725 for securing the prosthesis. Some embodiments may include an adapter, not shown, that adapts connector system 725 to a particular prosthesis, different adapters allowing use of pulse transfer assembly 705 with different prosthesis.

Central assembly 950 includes a support 975 coupled to outer housing 735 by a connector and receives double anvil 955 which moves freely within support 975. The heads of the upper transfer assembly and the lower transfer assembly are disposed within support 975 and arranged to strike corresponding ends of double anvil 955 during pulse generation.

In operation, oscillation engine 710 generates pulses that are transferred via pulse transfer assembly 705 to the prosthesis secured by connector system 725. The pulse transfer assembly 705, via upper transfer assembly 940, receives the generated pulses using transfer rod 965. Transfer rod 965 of upper transfer assembly 940 moves within support 960 of upper transfer assembly 940 to communicate pulses to double anvil 955 moving within support 975. Double anvil 955, in turn, communicates pulses to transfer rod 965 of lower transfer assembly 945 to produce vibratory motion of a prosthesis secured to connector system 725. Transfer rods 965 move, in this illustrated embodiment, primarily longitudinally/axially within outer housing 735 (a longitudinal axis defined as extending between proximate end 715 and distal end 720. In this way, the surgeon may use outer housing 735 as a hand hold when installing and/or positioning the vibrating prosthesis.

The use of discrete transfer portions (e.g., upper, central, and lower transfer assemblies) for pulse transfer assembly 705 may allow a form of loose coupling between oscillation engine 710 and a secured prosthesis. In this way pulses from oscillation engine 710 are converted into a vibratory motion of the prosthesis as it is urged into the bone during operation. Some embodiments may provide a stronger coupling by directly securing one component to another, or substituting a single component for a pair of components.

The embodiment of FIG. 7 has demonstrated insertion of a prosthetic cup into a bone substitute substrate with ease and a greatly reduced force as compared to use of a mallet and tamp, especially as no impaction was required. While the insertion was taking place and vibrational motion was present at the prosthesis, the prosthesis could be positioned with relative ease by torqueing on a handle/outer housing to an exact desired alignment/position. The insertion force is variable and ranges between 20 to 800 pounds of force. Importantly the potential for use of significantly smaller forces in application of the prosthesis (in this case the acetabular prosthesis) in bone substrate with the present invention is demonstrated to be achievable.

Installation system 700 may include an oscillation engine producing pulses at approximately 60 Hz. System 700 operated at 60 Hz. In testing, approximately 4 seconds of operation resulted in a desired insertion and alignment of the prosthesis (meaning about 240 cycles of the oscillation engine). Conventional surgery using a mallet striking a tamp to impact the cup into place is generally complete after 10 blows of the mallet/hammer.

Experimental

System 700 was tested in a bone substitute substrate with a standard Zimmer acetabular cup using standard technique of under reaming a prepared surface by 1 mm and inserting a cup that was one millimeter larger. The substrate was chosen as the best option available to study this concept, namely a dense foam material. It was recognized that certain properties of bone would not be represented here (e.g. less of an ability of the bone substrate to stretch before failure).

FIG. 7 demonstrated easy insertion and positioning of the prosthetic cup within the chosen substrate. We were able to move the cup in the substrate with relative ease. There was no requirement for a mallet or hammer for application of a large impact. These experiments demonstrated that the prosthetic cups could be inserted in bone substitute substrates with significantly less force and more control than what could be done with blows of a hammer or mallet. We surmise that the same phenomena can be reproduced in human bone. We envision the prosthetic cup being inserted with ease with very little force.

Additionally, we believe that simultaneously, while the cup is being inserted, the position of the cup can be adjusted under direct visualization with any intra-operative measurement system (navigation, fluoroscopy, and the like). This invention provides a system that allows insertion of a prosthetic component with NON-traumatic force (insertion) as opposed to traumatic force (impaction).

Experimental Configuration—System 700

Oscillation engine 710 included a Craftsman GO Hammerhead nailed used to drive fairly large framing nails into wood in confined spaces by applying a series of small impacts very rapidly in contrast to application of few large impacts.

The bone substitute was 15-pound density urethane foam to represent the pelvic acetabulum. It was shaped with a standard cutting tool commonly used to clean up a patient's damaged acetabulum. A 54 mm cup and a 53 mm cutter were used in testing.

In one test, the cup was inserted using a mallet and tamp, with impaction complete after 7 strikes. Re-orientation of the cup was required by further strikes on a periphery of the cup after impaction to achieve a desired orientation. It was qualitatively determined that the feel and insertion were consistent with impaction into bone.

An embodiment of system 700 was used in lieu of the mallet and tamp method. Several insertions were performed, with the insertions found to be much more gradual; allowing the cup to be guided into position (depth and orientation during insertion). Final corrective positioning is easily achievable using lateral hand pressure to rotate the cup within the substrate while power was applied to the oscillation engine.

Further testing using the sensor included general static load detection done to determine the static (non-impact) load to push the cup into the prepared socket model. This provided a baseline for comparison to the impact load testing. The prosthesis was provided above a prepared socket with a screw mounted to the cup to transmit a force applied from a bench vise. The handle of the vice was turned to apply an even force to compress the cup into the socket until the cup was fully seated. The cup began to move into the socket at about an insertion force of ~200 pounds and gradually increased as diameter of cup inserted into socket increased to a maximum of 375 pounds which remained constant until the cup was fully seated.

Installation system 700 was next used to install the cup into a similarly prepared socket. Five tests were done, using different frame rates and setup procedures, to determine how to get the most meaningful results. All tests used a 54 mm acetabular Cup. The oscillation engine ran at an indicated 60 impacts/second. The first two tests were done at 2,000 frames/second, which wasn't fast enough to capture all the impact events but helped with designing the proper setup. Test 3 used the oscillation engine in an already used socket, 4,000 frames per second. Test 4 used the oscillation engine in an unused foam socket at 53 mm, 4,000 frames per second.

Test 3: In already compacted socket, the cup was pulsed using the oscillation engine and the pulse transfer assembly. Recorded strikes between 500 and 800 lbs., with an average recorded pulse duration 0.8 Ms.

Test 4: Into an unused 53 mm socket, the cup was pulsed using the oscillation engine and the pulse transfer assembly. Recorded impacts between 250 and 800 lbs., and an average recorded pulse duration 0.8 Ms. Insertion completed in 3.37 seconds, 202 impact hits.

Test 5: Into an unused 53 mm socket, the cup was inserted with standard hammer (for reference). Recorded impacts between 500 and 800 lbs., and an average recorded pulse duration 22.0 Ms. Insertion completed in 4 seconds using 10 impact hits for a total pressure time of 220 Ms. This test was performed rapidly to complete it in 5 seconds for good comparability with tests 3 and 4 used 240 hits in 4 seconds, with a single hit duration of 0.8 MS, for a total pressure time of 192 Ms.

Additionally, basic studies can further be conducted to correlate a density and a porosity of bone at various ages (e.g., through a cadaver study) with an appropriate force range and vibratory motion pattern required to insert a cup using the present invention. For example, a surgeon will be able to insert sensing equipment in patient bone, or use other evaluative procedures, (preoperative planning or while performing the procedure for example) to assess porosity and density of bone. Once known, the density or other bone characteristic is used to set an appropriate vibratory pattern including a force range on an installation system, and thus use a minimal required force to insert and/or position the prosthesis.

BMD is a "must have" device for all medical device companies and surgeons. Without BMD the Implantation problem is not addressed, regardless of the recent advances in technologies in hip replacement surgery (i.e.; Navigation, Fluoroscopy, MAKE/robotics, accelerometers/gyro meters, etc.). Acetabular component (cup) positioning remains the biggest problem in hip replacement surgery. Implantation is the final step where error is introduced into the system and heretofore no attention has been brought to this problem. Current technologies have brought significant awareness to the position of the implants within the pelvis during surgery, prior to impaction. However, these techniques do not assist in the final step of implantation.

BMD allows all real-time information technologies to utilize (a tool) to precisely and accurately implant the acetabular component (cup) within the pelvic acetabulum. BMD device coupled with use of navigation technology and fluoroscopy and (other novel measuring devices) is the only device that will allow surgeons from all walks of life, (low volume/high volume) to perform a perfect hip replacement with respect to acetabular component (cup) placement. With the use of BMD, surgeons can feel confident that they are doing a good job with acetabular component positioning, achieving the "perfect cup" every time. Hence the BMD concept eliminates the most common cause of complications in hip replacement surgery which has forever plagued the surgeon, the patients and the society in general.

It is known to use ultrasound devices in connection with some aspects of THR, primarily for implant removal (as some components may be installed using a cement that may be softened using ultrasound energy). There may be some suggestion that some ultrasonic devices that employ "ultrasound" energy could be used to insert a prosthesis for final fit, but it is in the context of a femoral component and it is believed that these devices are not presently actually used in the process). Some embodiments of BMD, in contrast, can simply be a vibratory device (non-ultrasonic, others ultrasonic, and some hybrid impactful and vibratory), and is more profound than simply an implantation device as it is most preferably a positioning device for the acetabular component in THR. Further, there is a discussion that ultrasound devices may be used to prepare bones for implanting a prosthesis. BMD may address preparation of the bone in some aspects of the present invention.

Some embodiments BMD include devices that concern themselves with proper installation and positioning of the prosthesis (e.g., an acetabular component) at the time of implanting of the prosthesis. Very specifically, it uses some form of vibratory energy coupled with a variety of "real-time measurement systems" to POSITION the cup in a perfect alignment with minimal use of force. A prosthesis, such as for example, an acetabular cup, resists insertion. Once inserted, the cup resists changes to the inserted orientation. The BMDs of the present invention produce an insertion vibratory motion of a secured prosthesis that reduces the forces resisting insertion. In some implementations, the BMD may produce a positioning vibratory motion that reduces the forces resisting changes to the orientation. There are some implementations that produce both types of motion, either as a single vibratory profile or alternative profiles. In the present context for purposes of the present invention, the vibratory motion is characterized as "floating" the prosthesis as the prosthesis can become much simpler to insert and/or re-orient while the desired vibratory motion is available to the prosthesis. Some embodiments are described as producing vibrating prosthesis with a predetermined vibration pattern. In some implementations, the predetermined vibration pattern is predictable and largely completely defined in advance. In other implementations, the predetermined vibration pattern includes randomized vibratory motion in one or more motion freedoms of the available degrees of freedom (up to six degrees of freedom). That is, whichever translation or rotational freedom of motion is defined for the vibrating prosthesis, any of them may have an intentional randomness component, varying from large to small. In some cases, the randomness component in any particular motion may be large and, in some cases, predominate the motion. In other cases, the randomness component may be relatively small as to be barely detectable.

A tool, among others, that may support the force measurement includes an axially-impactful Behzadi Medical Device (BMD4). The BMD4 may include a moveable hammer sliding axially and freely along a rod. The rod may include a proximal stop and a distal stop. These stops that may be integrated into rod allow transference of force to rod when the hammer strikes the distal stop. At a distal end of the rod, the device includes an attachment system for a prosthesis. For example, when the prosthesis includes an acetabular cup having a threaded cavity, the attachment system may include a complementary threaded structure that screws into the threaded cavity. The illustrated design of the device allows only a perfect axial force to be imparted. The surgeon cannot deliver a blow to the edge of an impaction plate. Therefore, the design of this instrument is in and of itself protective, eliminating a problem of "surgeon's mallet hitting on the edge of the impaction plate" or other mis-aligned force transference, and creating undesirable torques, and hence unintentional mal-alignment of the prosthesis from an intended position/orientation. This embodiment may be modified to include a vibratory engine as described herein.

The embodiment may include a pressure sensor to provide feedback during installation. With respect to management of the vibration/force required for some of these tasks, it is noted that with current techniques (the use of the mallet) the surgeon has no indication of how much force is being imparted onto the implant and/or the implant site (e.g., the pelvis). Laboratory tests may be done to estimate what range of force should be utilized in certain age groups (as a rough guide) and then fashioning a device 1100, for example a modified sledgehammer or a cockup gun to produce just the right amount of force and/or producing a predetermined force of a known magnitude. Typically, the surgeon may use up to 2000N to 3000N of force to impact a cup into the acetabular cavity. Also, since some embodiments cannot deliver the force in an incremental fashion as described in association with the BMD3 device, the device may include a stopgap mechanism. Some embodiments of the BMD3 device have already described the application of a sensor in the body of the impaction rod. The device may include a sensing system/assembly embedded in the device, for example proximate the rod near the distal end, and used to provide valuable feedback information to the surgeon. The pressure sensor can let the surgeon know when the pressures seem to have maximized, whether used for the insertion of an acetabular cup, or any other implant including knee and shoulder implants and rods used to fix tibia and femur fractures. When the pressure sensor is not showing an advance or increase in pressure readings and has plateaued, the surgeon may determine it is time to stop operation/impacting. An indicator, for example an alarm can go off or a red signal can show when maximal peak forces are repeatedly achieved. As noted above, the incorporated patents describe a presence of a pressure sensor in an installation device, the presence of which was designed as part of a system to characterize an installation pulse pattern communicated by a pulse transfer assembly. The disclosure here relates to a pressure sensor provided not to characterize the installation vibration/pulse pattern but to provide an in-situ feedback mechanism to the surgeon as to a status of the installation, such as to reduce a risk of fracturing the installation site. Some embodiments may also employ this pressure sensor for multiple purposes including characterization of an applied pulse pattern such as, for example, when the device includes automated control of an impacting engine coupled to the hammer. Other embodiments of this invention may dispose the sensor or sensor reading system within a handle or housing of the device rather than in the central rod or shaft.

Previous work has sought to address the two problems noted above culminating in a series of devices identified as BMD2, BMD3, and BMD4, collectively herein representative of examples of an insertion agency. Each of these systems attempts to address the two problems noted above with different and novel methods.

The BMD2 concept proposed a system of correcting a cup (acetabular implant) that had already been implanted in a mis-aligned position. It basically involves a gun like tool with a central shaft and peripheral actuators, which attaches to an already implanted cup with the use of an adaptor. Using computer navigation, through a series of calculations, pure points (specifically defined) and secondary points on the edge of the cup are determined. This process confers positional information to the edge of the cup. The BMD2 tool has actuators that correspond to these points on the cup, and through a computer program, the appropriate actuators impact on specific points on the edge of the cup to adjust the position of the implanted cup. The surgeon dials in the desired alignment and the BMD2 tool fires the appropriate actuators to realign the cup to the perfect position.

In BMD3, we considered that vibratory forces may be applied in a manner to disarm frictional forces in insertion of the acetabular cup into the pelvis. We asked the following questions: Is it possible to insert and position the cup into the pelvis without high energy impacts? Is it possible to insert the cup using vibratory energy? Is insertion and simultaneous alignment and positioning of the cup into the pelvis possible? BMD3 prototypes were designed and the concept of vibratory insertion was proven. It was possible to insert the cup with vibratory energy. The BMD3 principle involved the breaking down of the large momentum associated with the discrete blows of the mallet into a series of small taps, which in turn did much of the same work incrementally, and in a stepwise fashion. We considered that this method allowed modulation of force required for cup insertion. In determining the amount of force to be applied, we studied the resistive forces involved in a cup/cavity interaction. We determined that there are several factors that produce the resistive force to cup insertion. These include bone density (hard or soft), cup geometry (spherical or elliptical), and surface roughness of the cup. With the use of BMD3 vibratory insertion, we demonstrated through FEM studies, that the acetabulum experiences less stress and deformation and the cup experiences a significantly smoother sinking pattern. We discovered the added benefit of ease of movement and the ability to align the cup with the BMD3 vibratory tool. During high frequency vibration the frictional forces are disarmed in both effective and realistic ways, (see previous papers-periodic static friction regime, kinetic friction regime). We have also theorized that certain "mode shapes" (preferred directions of deformation) can be elicited with high frequency vibration to allow easy insertion and alignment of the cup. The pelvis has a resonant frequency and is a viscoelastic structure. Theoretically, vibrations can exploit the elastic nature of bone and its dynamic response. This aspect of vibratory insertion can be used to our advantage in cup insertion and deserves further study. Empirically, the high frequency aspect of BMD3 allows easy and effortless movement and insertion of the cup into the pelvis. This aspect BMD3 is clinically significant allowing the surgeon to align the cup in perfect position while the vibrations are occurring.

The BMD4 idea was described to address the two initial problems (uncontrolled force and undesirable torques) in a simpler manner. The undesirable torque and mis-alignment problem from mallet blows were neutralized with the concept of the "slide-hammer" which only allows axial exertion of force. With respect to the amount of force, BMD4 allowed the breaking down of the large impaction forces (associated with the use of the mallet) into quantifiable and smaller packets of force. The delivery of this force occurs through a simple slide-hammer, cockup gun, robotic tool, electric or pneumatic gun (all of which deliver a sliding mass over a central coaxial shaft attached to the impaction rod and cup. In the BMD4 paper we described two "stop gap" mechanisms to protect the pelvis from over exertion of force. We described a pressure sensor in the shaft of the BMD4 tool that monitors the force pressure in the (tool/cup system). This force sensor would determine when the pressure had plateaued indicating the appropriate time to stop the manual impacts. We also described a pitch/sound sensor in the room, attached to the gun or attached to the pelvis that would assess when the pitch is not advancing, alerting the surgeon to stop applying force. These four aspects of BMD4 (coaxially of the gun, quantification and control of the force, a force sensor, a sound sensor) are separated and independent functions which can could be used alone or in conjunction with each other.

We also recommended that BMD4's (coaxiality and force control function) and BMD3's (vibratory insertion) be utilized for application of femoral and humeral heads to trunnions, to solve the trunnionosis problem.

Materials and Methods: During our development, we evaluated different aspects of the BMD3 and BMD4 prototypes. With BMD3 concept we sought to study several aspects of vibratory insertion:

1. The ultimate effect of frequency on cup insertion.
2. The range of impact forces achievable with vibratory insertion.
3. The effect of frequency and vibratory impaction forces on cup insertion and (extraction forces measured to assess the quality of insertion).

With Respect to BMD4 we studied the various aspects of "controlled impaction" utilizing Drop Tests (dynamic testing) and Instron Machine (static testing) to determine the behavior of cup/cavity interaction.

Results:
BMD3

Preliminary results suggest that vibratory insertion of the cup into a bone substitute is possible. It is clear that vibratory insertion at higher frequencies allow easy insertion and alignment of the cup in bone.

It is unclear as to how much higher frequencies contribute to the depth and quality of insertion, as measured by the extraction force, particularly as the cup is inserted deeper into the substrate.

We determined that with vibrational insertion, the magnitude of impaction force is limited and dependent on other mechanical factors such as frequency of vibration and the dwell time. So far 400 lbs. of force have been achieved with the BMD/BE prototype, 250 lbs. of force have been achieved with the auto hammer prototype, and 150 lbs. of force have been achieved by the pneumatic prototype. Further work is underway to determine the upper limit of achievable forces with the Vibrational tools.

During our study of Vibrational insertion, we also discovered that vibrational insertion can be unidirectional or bidirectional. For insertion of the cup into a substrate it was felt that unidirectional vibratory insertion (in a positive direction) is ideal. We discovered that unidirectional vibratory withdrawal and bidirectional vibration have other applications such as in revision surgery, preparation of bone, and for insertion of bidirectional prosthetic cups. The directionality of the BMD3 vibratory prototype and its applications will be further discussed in additional applications.

BMD4

With respect to controlled impacts we sought to understand the cup/cavity interaction in a more comprehensive way. We wanted to discover the nature of the resistive forces involved in a cup/cavity interaction. We felt it was necessary for us to know this information in order to be able to produce the appropriate amount of force for both BMD3 "vibratory insertion" and BMD4 "controlled impaction". We proposed and conducted dynamic Drop tests and static Instron tests to evaluate the relationship between the cup and the cavity. Instron testing is underway and soon to be completed. The drop tests were conducted using a Zimmer continuum 62 mm cup and 20 lbs. urethane foam. Multiple drop tests were conducted at various impaction forces to evaluate the relationship between applied force (TMIF) and displacement of the cup, and the quality of insertion (Extraction Force). We discovered that for insertion of a cup into a cavity the total resistive force can be generally represented by an exponential curve. We have termed this resistive force the FR, which is determined by measuring the relationship of applied force (TMIF) and cup insertion for any particular (cup/cavity) system. FR is a function of several factors including the spring like quality of bone which applies a compressive resistive force (Hooke's law F=kx) to the cup, the surface roughness's of the cup, an amount of under reaming, and the geometry of the cup (elliptical v spherical).

Definitions: FR=Force Resistance (total resistive force to cup insertion over full insertion of the cup into bone substitute); TMIF=Theoretical Maximum Impact Force (external force applied to the system) to accomplish cup insertion; and mIF=measured Impact Force (force measured within the system) (as measured on the BMD3 and BMD4) tools.

| BMD/BE | vibratory prototype |
|---|---|
| Auto hammer | vibratory prototype |
| Pneumatic | vibratory prototype |

Evaluation of the drop test data reveals a nonlinear (exponential) curve that represents FR. We contemplated that the cup/cavity system we used (62 m Continuum cup and 20 lb. urethane foam) has a specific profile or "cup print", and that this profile was important to know in advance so that application of force can be done intelligently.

We observed the general shape of FR to be non-linear with three distinct segments to the curve, which we have termed A, B, and C. In section A the resistive force is low (from 100 to 350 lbs.) with a smaller slope. In section A, if an applied force (TMIF) greater than this FR is applied, it can produce up to 55% cup insertion and 30% extraction force. A TMIF that is tuned to cross FR at the A range is at risk for poor seating and pull out. In section B the resistive forces range from 500 lbs to 900 lbs. The slope rises rapidly and is significantly larger than in section A (as expected in an exponential curve). In section B, if a TMIF greater than this FR is applied, it can produce between 74% to 90% cup insertion and between 51% to 88% extraction force. We name this section the "B cloud", to signify that the applied force (TMIF) should generally be tuned to this level to obtain appropriate insertion with less risk for fracture and or pull out, regardless of whether the TMIF is applied by a BMD3 or BMD4 tool. In section C the curve asymptotes, with small incremental increase in cup insertion and large increases in extraction force. The clinical value of the higher extraction force is uncertain with increased risk of fracture. A TMIF that is tuned to cross the FR at the C range is high risk for fracture and injury to the pelvis.

Figure 12:
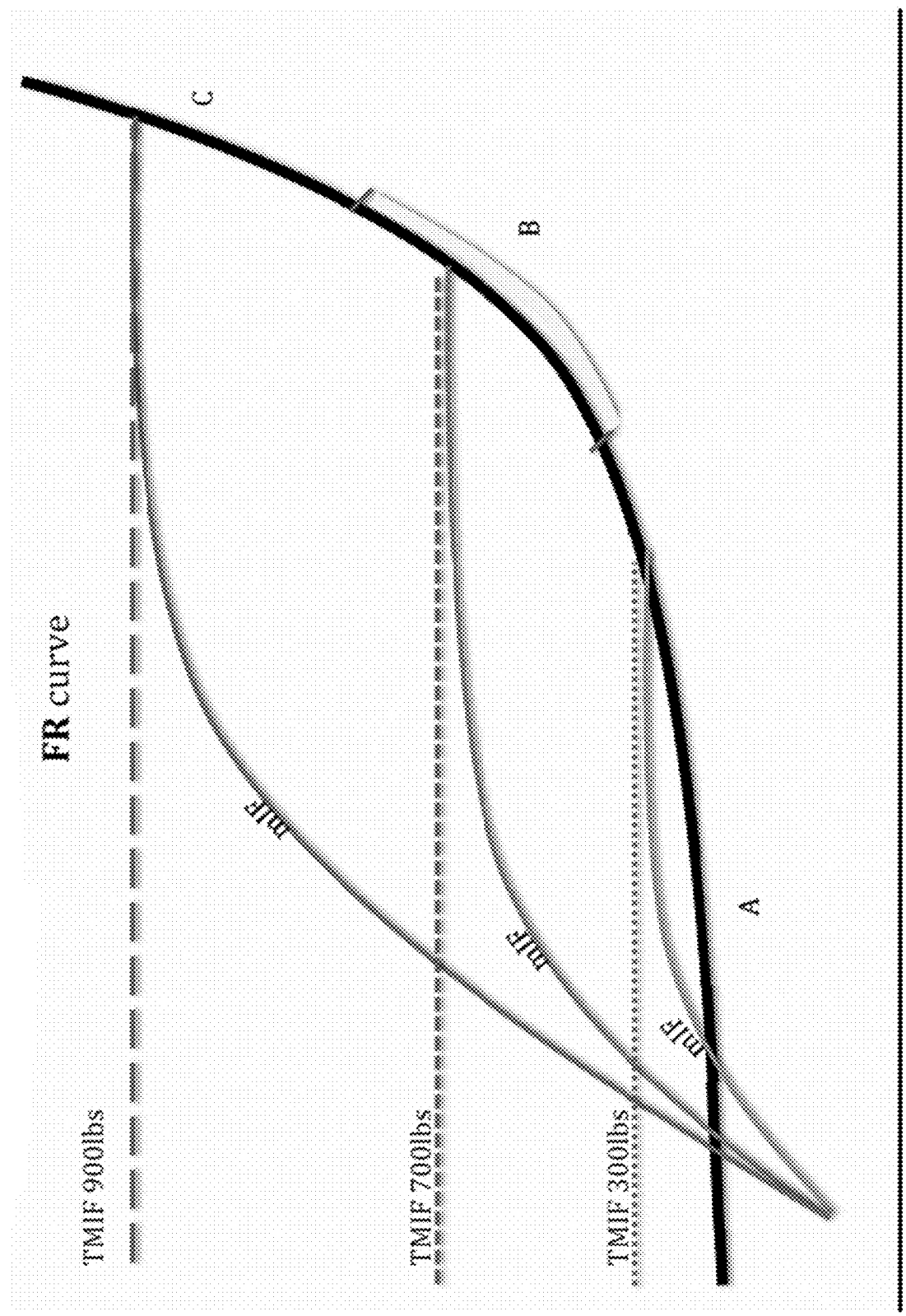
FIG. 12 illustrates a Force Resistance (FR) curve.

FIG. 12 relates to a Behzadi Medical Device (BMDX) which may combine vibratory and axial impactful forces from BMD3 and BMD4 among other options; and FIG. 12 illustrates a Force Resistance (FR) curve for various experimental configurations, for example, force as a function of distance or displacement.

DISCUSSION

The FR curve represents a very important piece of information. To the surgeon the FR curve should have the same significance that a topographical map has to a mountaineer. Knowing the resistive forces involved in any particular cup/cavity interaction is desirable in order to know how much force is necessary for insertion of the cup. We believe that in vitro, all cup/cavity interactions have to be studied and qualified. For example, it is important to know if the same 62 mm Continuum cup we used in this experiment is going to be used in a 40-year-old or 70-year-old person. The variables that will determine FR include bone density which determines the spring like quality of bone that provides compression to the cup, the geometry of the cup, an amount of under reaming, and the surface roughness of the cup. Once the FR for a particular cup and bone density is known, the surgeon is now armed with information he/she can use to reliably insert the cup. This would seem to be a much better way to approach cup insertion than banging clueless on an impaction rod with a 4 lbs mallet. Approaching FR with an eye for the B range will assure that the cup is not going to be poorly seated with risk of pullout or too deeply seated with a risk of fracture.

We have contemplated approaching FR with both vibratory (BMD3) insertion and controlled (BMD4 impaction) among other devices. Each of these systems has advantages and disadvantages that continue to be studied and further developed.

For example, we believe that vibratory insertion with the current BMD3 prototypes have the clear advantage of allowing the surgeon ease of movement and insertion. The surgeon appears to be able to move the cup within the cavity by simple hand pressure to the desired alignment. This provides the appearance of a frictionless state. However, to date we have not quite been able to achieve higher forces with the BMD3 tools. So far, we have been able to achieve up to 150 lb. (pneumatic), 250 (auto hammer), and 400 lb. (BMD/BE) in our vibratory prototypes. This level of applied force provides submaximal level of insertion and pull out force. We believe that ultimately, higher forces can be achieved with the vibratory BMD3 tools (500 to 900 lbs) which will provide for deep and secure seating.

With regards to this concern, we have contemplated a novel approach to address the current technological deficits. We propose a combination of BMD3 vibratory insertion with controlled BMD4 impaction. The BMD3 vibratory tool (currently at 100 lbs. to 400 lbs) is used to initiate the first phase of insertion allowing the surgeon to easily align and partially insert the prosthesis with hand pressure, while monitoring the alignment with the method of choice (A-frame, navigation, C-arm, IMU). The BMD4 controlled impaction is then utilized to apply quantifiable packets of force (100 lbs. to 900 lbs) to the cup to finish the seating of the prosthesis in the B range of the FR curve. This can be done either as a single step fashion or "walking up the FR curve" fashion.

Alternatively, BMD4 controlled impaction can be utilized to insert the cup without the advantage of BMD3 tool. The BMD4 technique provides the ability to quantify and control the amount of applied force (TMIF) and provides coaxiality to avoid undesirable torques during the impaction. It is particularly appealing for robotic insertion where the position of the impaction rod is rigidly secured by the robot.

We have contemplated that the BMD4 controlled impaction can be utilized in two separate techniques.

The first technique involves setting the impaction force within the middle of the B Cloud where 74% to 90% insertion and 51% to 88% extraction forces could be expected, and then impacting the cup. The BMD4 tool acts through the slide hammer mechanism to produce a specific amount of force (for example 600 lbs) and deliver it axially. This can be considered a single step mechanism for use of BMD4 technique.

The second method involves "walking the forces" up the FR curve. In this system the applied force (TMIF) is provided in "packets of energy". For example, the BMD4 gun may create 100 lbs packets of force. It has an internal pressure sensing mechanism that allows the tool to know if insertion is occurring or not. A force sensor and a corresponding algorithm within the BMD4 tool is described herein. The force sensor monitors the measured impact force (mIF) and the corresponding change in mIF within the system. As we have described before, when impacts are applied to an "inelastic" system, energy is lost at the interface as insertion occurs and heat is produced. This loss of energy is measured and calculated in the (change) or slope of mIF. Consecutive mIF s have to be measured and compared to previous mIFs to determine if insertion is occurring. As long as insertion is occurring impactions will continue. When the change in mIF approaches zero, insertion is not occurring, there is no dissipation of energy within the system the slope or (change) in mIF has approached zero. At this point the cup and cavity move together as a rigid system (elastic), and all the kinetic energy of TMIF is experienced by the cup/cavity system and mIF is measured to be the same as TMIF. When insertion is not occurring mIF has approached TMIF and change in mIF has approached zero.

At this point the next step is taken and TMIF is increased, for example by a packet of 100 lbs. The subsequent mIF measurements are taken and if the slope (change) in mIF is high, insertion is occurring with the new TMIF, therefore impacts should continue until the change in mIF approaches zero again.

Conversely, if an increase in TMIF results in an increase in mIF but not the change (slope) in mIF, we know the cup is no longer inserting and has reached its maximum insertion point. We should point out that when the cup stops inserting, this also the point where FR exceeds TMIF. In this manner, we have contemplated an algorithm that allows for monitoring of the forces experienced in the system. Based on this algorithm, a system is created in which the surgeon can walk the TMIF up the FR curve while being given real-time feedback information as to when to stop impaction.

The general idea is that at some point in time the cup will no longer insert (even though not fully seated). This algorithm determines when no further insertion is occurring. The surgeon will be content to stop impaction in the B cloud range of the FR curve.

We have also discovered that mIF is related to TMIF+FR. The value of TMIF is known. The value of mIF is measured. The FR can be calculated live during insertion by the BMD3 and BMD4 tools and shown to the surgeon as a % or (probability of fracture). This calculation and algorithm could be very significant.

A few words on Alignment:

We have so far proposed that the BMD3 vibratory tool be used to insert the cup under monitoring by current alignment techniques (navigation, Fluoroscopy, A-frame). We have now devised a novel system, which we believe will be the most efficacious method of monitoring and assuring alignment. This system relies of Radlink (X-rays) and PSI (patient specific models) to set and calibrate the OR space as the first step.

As a second step, it utilizes a novel technique with use of IMU technology to monitor the movement of the reamers, tools (BMDs) and impaction rods. This is discussed in a separate paper. Needs to be written up.

Summary and Recommendations for BMD/BE project.

1. We propose a novel system of inserting and aligning the acetabular cup in the human pelvic bone. This technique involves combining aspects of the BMD3 and BMD4 prototypes, initially utilizing BMD3 vibratory insertion to partially insert and perfectly align the acetabular cup into the pelvis. Subsequently switching to the BMD4 controlled impaction technique to apply specific quantifiable forces for full seating and insertion. In this manner we are combining the proven advantages of the vibratory insertion prototype with the advantages of the controlled impaction prototype.

2. We have described a force sensing system within the BMD tool with capacity to measure the force experienced by the system (mIF) and calculate the change in mIF with respect to time or number of impacts. This system provides a feedback mechanism for the BMD tools as to when impaction should stop.

3. We have described the FR curve which is a profile (cup print) of any cup/cavity interaction. And have recommended that this "cup print" for most cup/cavity interactions be determined in vitro to arm the surgeon with information necessary for cup insertion. We feel that every cup/cavity interaction deserves study to determine its FR profile. Once the FR is known, BMD3 and BMD4 tools can be used to intelligently and confidently apply force for insertion of the acetabular prosthesis.

4. We have described two methods for use of BMD4 controlled cup impaction a. Setting the TMIF to the middle of the B cloud (somewhere between 500 to 900 range for our FR) and producing a single stage impaction.

b. Producing sequential packets of increasing TMIF in order to walk TMIF up the FR curve. (Increasing packets of 100 lbs or 200 lbs)

5. We have also discovered that mIF is related to TMIF+FR. The value of TMIF is known. The value of mIF is measured. The FR can be calculated live during insertion by the BMD3 and BMD4 tools and shown to the surgeon as a % or (probability of fracture). This calculation and algorithm could be very significant in help the surgeon to insert the cup deeply without fracture.

Concept 5W and 1H:

1. Who: The surgeon; 2. What: Cup insertion; 3. When: When to increase the force and when to stop; 4. Where: PSI and Radlink to set and IMU to monitor alignment and position; 5. Why: Consistency for the surgeon and the patient; and 6. How: FR for every cup/cavity interaction, BMD3 and BMD4 tools.

Figure 13:
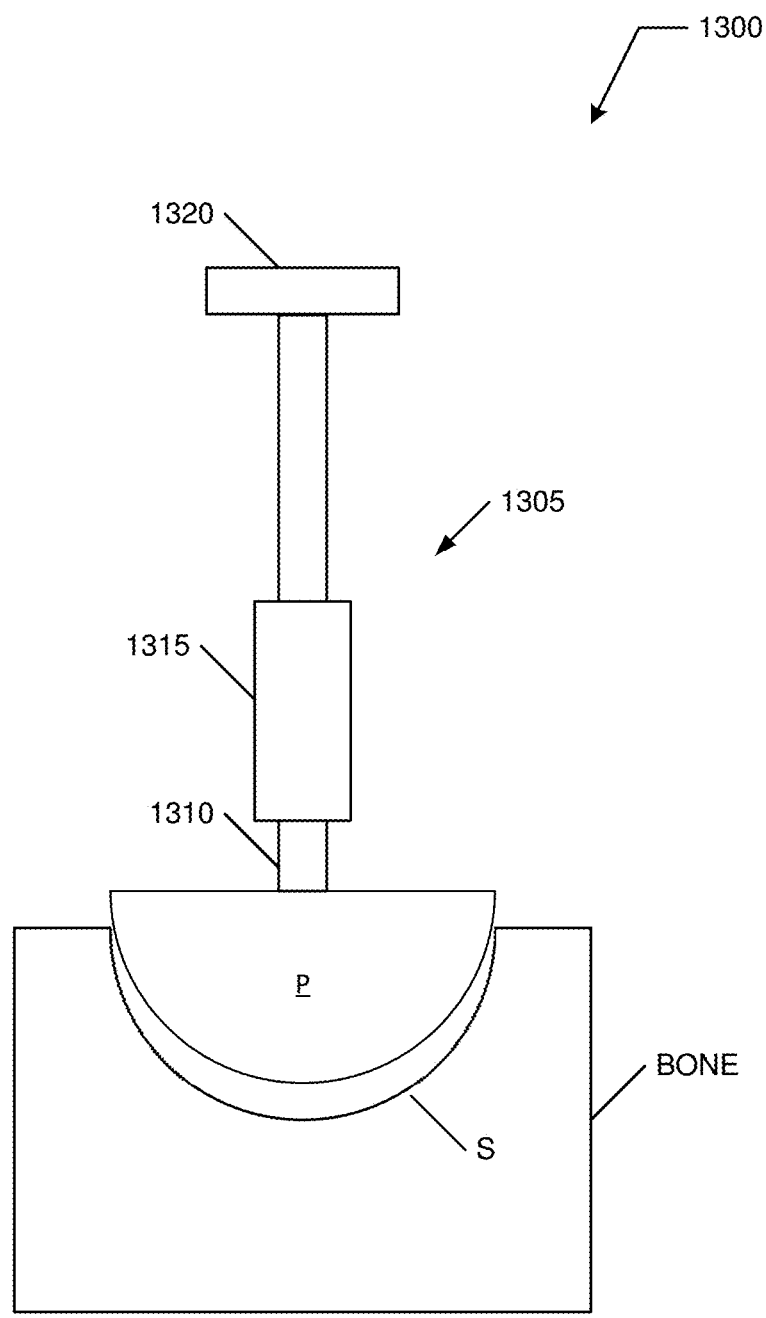
FIG. 13-FIG. 14 illustrate a general force measurement system for understanding an installation of a prosthesis into an installation site (e.g., an acetabular cup into an acetabulum during total hip replacement procedures)
Figure 14:
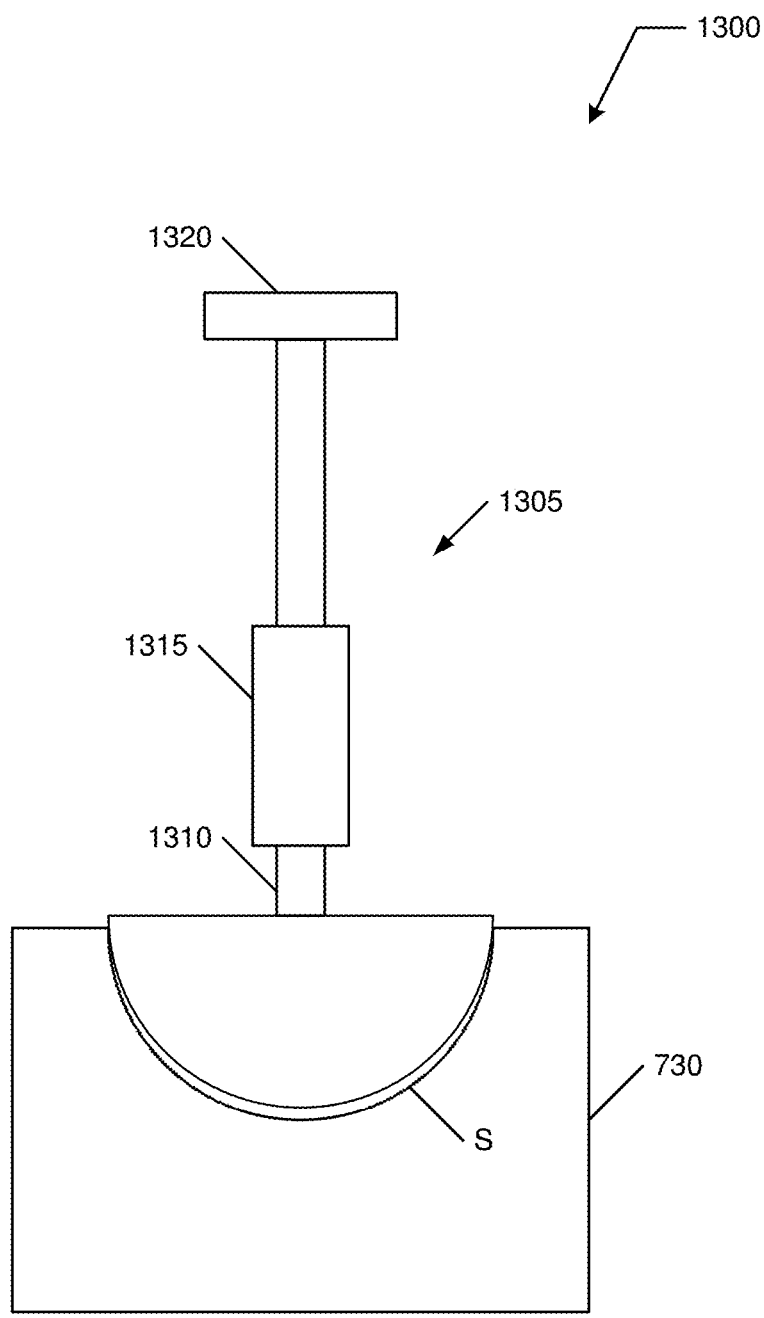

FIG. 13-FIG. 14 illustrate a general force measurement system 1300 for understanding an installation of a prosthesis P into an installation site S (e.g., an acetabular cup into an acetabulum during total hip replacement procedures); FIG. 13 illustrates an initial engagement of prosthesis P to a cavity at installation site S when prosthesis P is secured to a force sensing tool 1305; FIG. 14 illustrates a partial installation of prosthesis P 13 into the cavity by operation of force sensing tool 1305.

Tool 1305 includes an elongate member 1310, such as a shaft, rod, or the like. There may be many different embodiments but tool 1305 may include a mechanism for direct or indirect measurement of impact forces (mIF) such as by inclusion of an in-line sensor 1315. Further, tool 1305 allows for application of an external force applied to tool 1305. In some embodiments, another sensor 1320 may be used to measure this applied force as a theoretical maximum impact force (TMIF). In some cases, the TMIF is applied from outside and in other systems, the application is from tool 1305 itself. In some cases, there system 1300 has a priori knowledge of the force applied, or it can estimate it without use of sensor 1320. Depending upon an implementation, various user interface elements and controls may be included, including indicators for various measured, calculated, and/or determined status information.

During operation, as mIF begins to approach TMIF, then system 1300 understands that prosthesis P is not moving much, if any, in response to the TMIF (when it is kept relatively constant). An advantage to the mechanical tools is their ability to repeatably apply a known/predetermined force allowing for understanding of where the process is on an applicable FR curve for prosthesis P at installation site S. For example, in FIG. 14, the mIF, for a constant applied force, is closer to TMIF than in the case of FIG. 13.

The arrangement of FIG. 13-FIG. 14 may be implemented in many different ways as further explained herein for improving installation and reducing risk of fracture.

Figure 15:
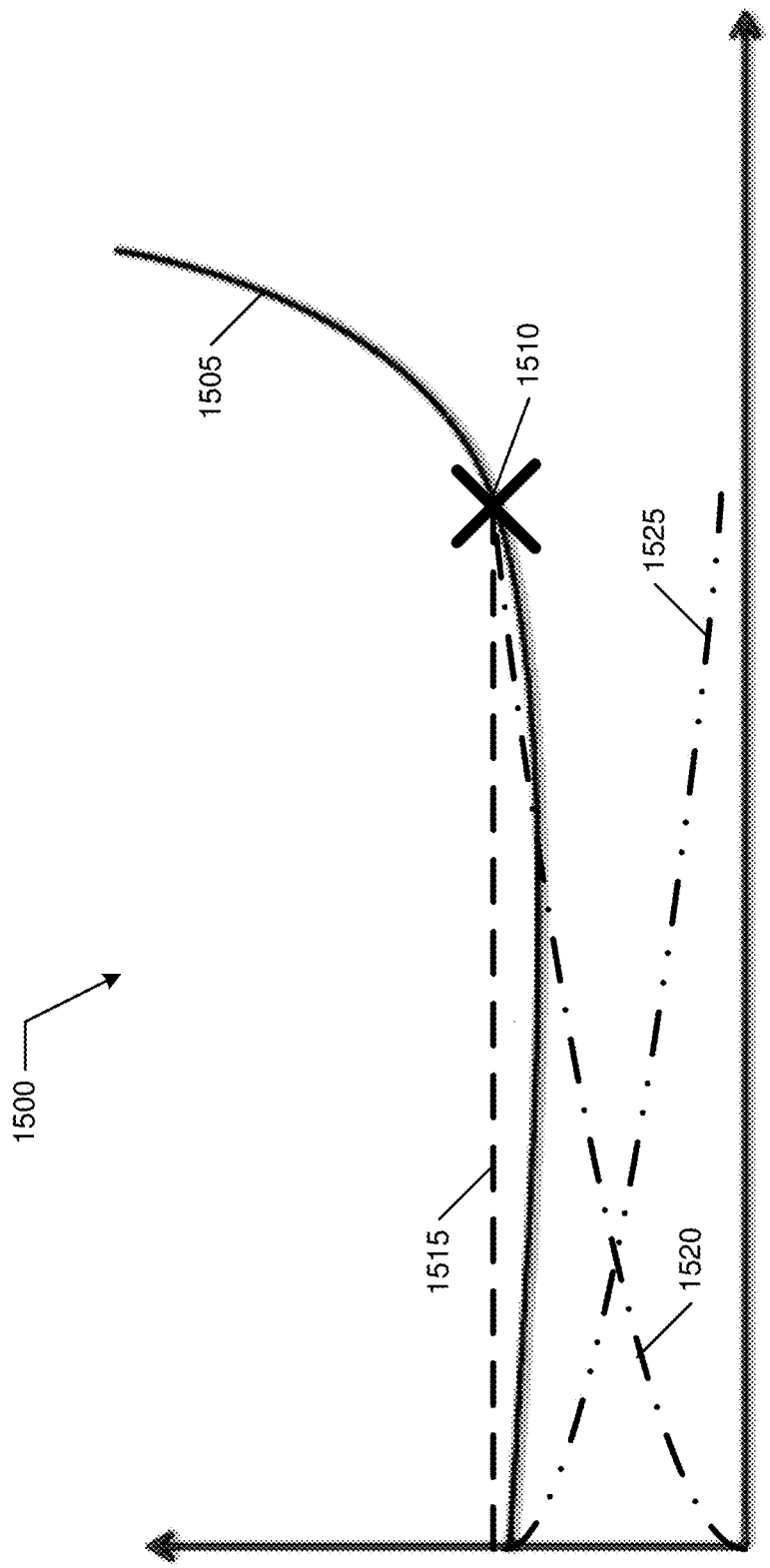
FIG. 15 illustrates a generalized FR curve illustrating various applicable forces implicated in operation of the tool in FIG. 13 and FIG. 14.

FIG. 15 illustrates a set of parameters and relationships for a force sensing system 1500 including a generalized FR curve 1505 visualizing various applicable forces implicated in operation of the tool in FIG. 13 and FIG. 14. Curve 1505 includes TMIF vs displacement of the implant at the installation site. Early, a small change of TMIF can result is a relatively large change in displacement. However, near the magic spot, the curve starts to transition where the implant is close to being seated and increases in TMIF may result in little displacement change. And as TMIF increases, the risk of fracture increases.

In FIG. 15, a particular state is illustrated by "X" a point 1510 on curve 1505. A particular constant value of TMIF 1515 is applied to the system and prosthesis P moves along curve 1505. A measured Impact Force (mIF) 1520 approaches the value of TMIF 1515 as prosthesis P approaches point 1510. A resultant curve 1525 illustrates a difference between TMIF 1515 and mIF 1520. As prosthesis P approaches point 1510, resultant curve 1525 provides a valuable, previously unavailable quantitative indication of how prosthesis P was responding to applied forces. It may be that the procedure stops at point 1510, or a new, larger value for TMIF is chosen to move prosthesis P along curve 1505. System 1500 provides the surgeon with knowledge of where on curve 1505 the prosthesis P resides and provides an indication of a risk of fracture versus improving seating of prosthesis P. By monitoring resultant curve 1525 in some form, system 1300 understands whether prosthesis is moving or has become seated. Each of these pieces of information is useful to system 1500 and/or the surgeon until completion of the process.

FIG. 16-FIG. 21 illustrate a first specific implementation of the system and method of FIG. 13-FIG. 15, FIG. 16 illustrates a representative plot 1600 of insertion force for a cup during installation. As prosthesis P is being installed by a system, device, process, or tool, each increment of the active installation will have an applicable minimum impact to overcome resistive (e.g., static friction) forces. The impact force required increases as the insertion depth of the cup increases due to larger normal forces acting on the cup/bone interface (see FIG. 16). There is a tension between seating and increased force though, as larger impact forces raise the risk of fracture of surrounding bone. The goal of the surgeon is to reach a sufficient insertion depth to generate acceptable cup stability (e.g., pull-out resistance), while minimizing forces imparted to the acetabulum during the process. The process does not want to terminate early as the prosthesis may too easily be removed and the process doesn't want to continue too long until the bone fractures. This area is believed to be in the beginning of the non-linear regime in the plot of FIG. 16, as higher forces begin to have a smaller incremental benefit to cup insertion (i.e. smaller incremental insertion depth with larger forces).

Figure 16:
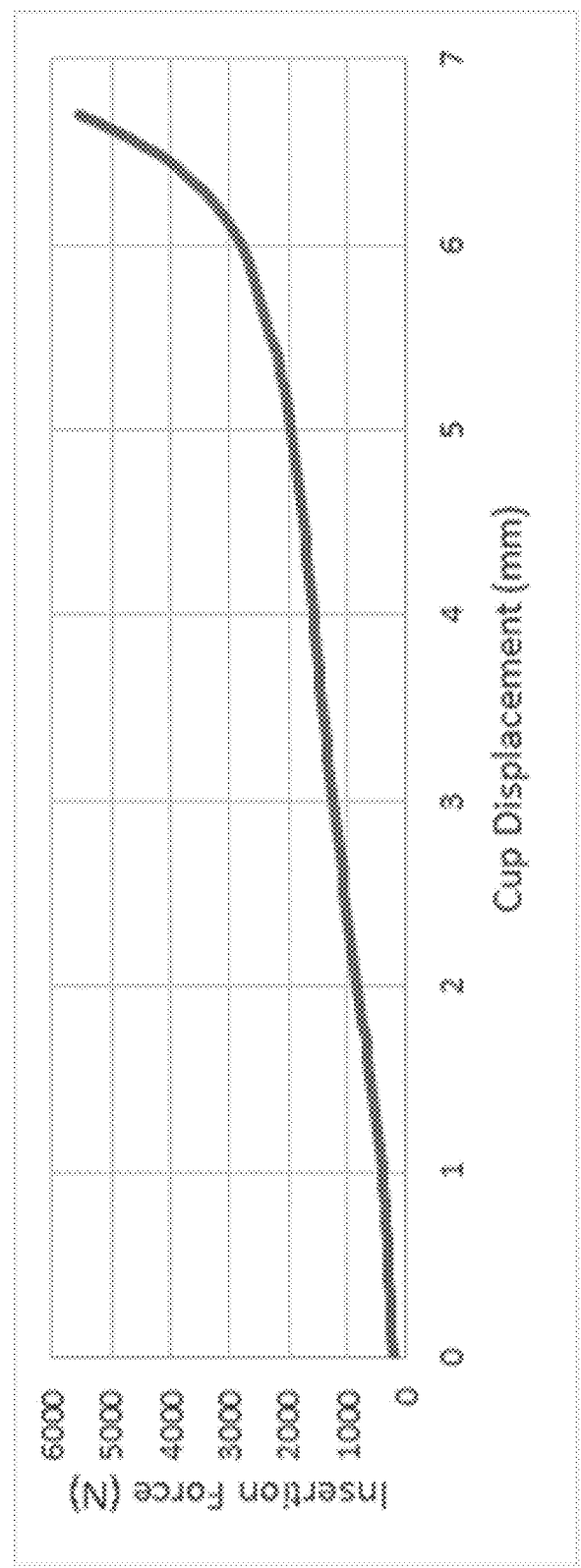
FIG. 16-FIG. 21 illustrate a first specific implementation of the system and method of FIG. 13-FIG. 15.
Figure 17:
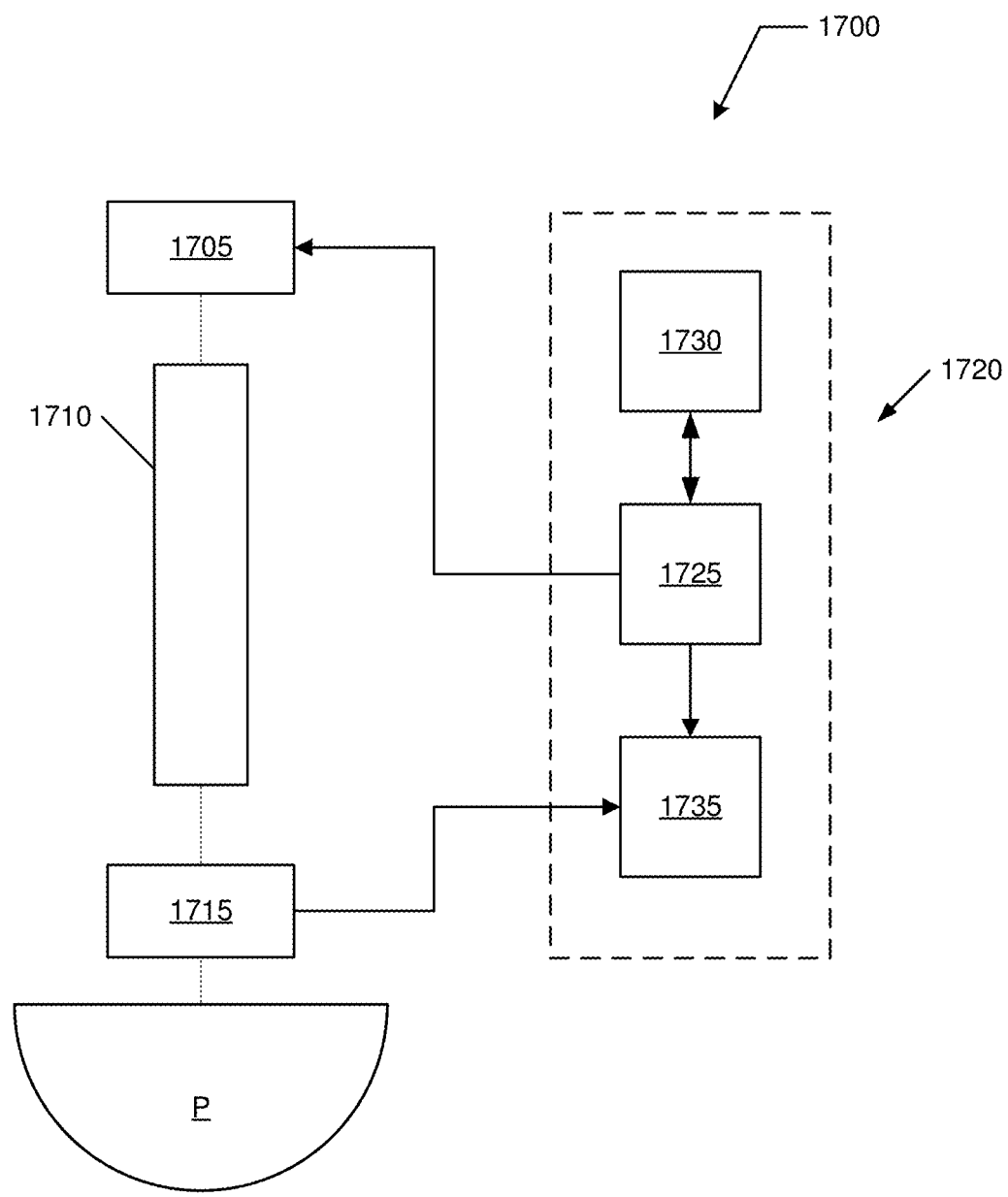

FIG. 17 illustrates a first particular embodiment of a BMDX force sensing tool 1700. Tool 1700 allows indirect measurement of a rate of insertion of an acetabular cup and may be used to control the impact force being delivered to the cup based upon control signals and the use of features of FIG. 16. Tool 1700 may include an actuator 1705, a shaft 1710, and a force sensor 1715. One representative method for force measurement/response would employ such a tool 1700. Similar to the impaction rod currently used by surgeons, tool 1700 would couple to an acetabular cup (prosthesis P) using an appropriate thread at the distal end of shaft 1710. Actuator 1705 would couple to a proximal end of shaft 1710, and create controlled impacts that would be applied to shaft 1710 and connected cup P. The magnitude of the impact(s) would be controlled by the surgeon through a system control 1720, such as a dial or other input mechanism on the device, or directly by the instrument's software. System control 1720 may include a microcontroller 1725 in two-way communication with a user interface 1730 and receiving inputs from a signal conditioner 1735 receiving data from force sensor 1715. Controller 1725 is coupled to actuator 1705 to set a desired impact value.

Figure 18:
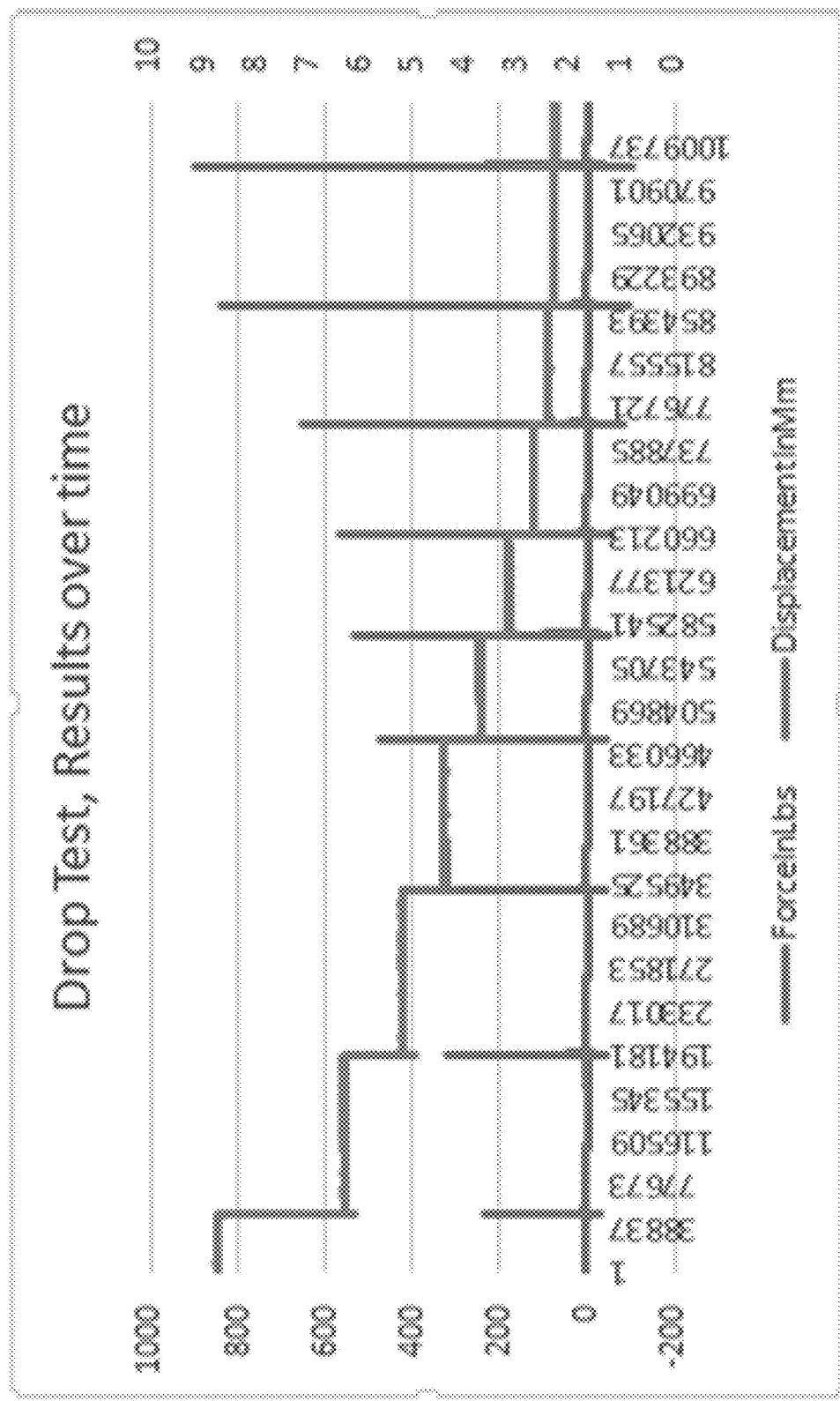

Force sensor 1715 may be mounted between the shaft 1710 and acetabular cup P. Sensor 1715 would be of a high enough sampling rate to capture the peak force generated during an actuator impact. It is known that for multiple impacts of a given energy, the resulting forces increase as the incremental cup insertion distance decreases, see, for example, FIG. 18. FIG. 18 illustrates a graph including results of a drop test over time which simulate use of tool 1700 installing cup P into bone.

This change in force given the same impact energy may be a result of the frictional forces between cup P and surrounding bone of the installation site. For the plot of FIG. 18, the initial impact has a slow deceleration of the cup due to its relatively large displacement, resulting in a low force measurement. The displacement decreases for subsequent impacts due to the increasing frictional forces between the cup and bone, which results in faster deceleration of the cup (the cup is decelerating from the same initial velocity over a shorter distance). This results in an increase in force measurement for each impact. The maximum force for a given impact energy will be when the cup P can no longer overcome, responsive to a given impact force from the actuating system, the resistive (e.g., static friction) forces from the surrounding bone. This results in a "plateau", where any subsequent impact will not change either the insertion of cup P or the force measured.

Figure 19:
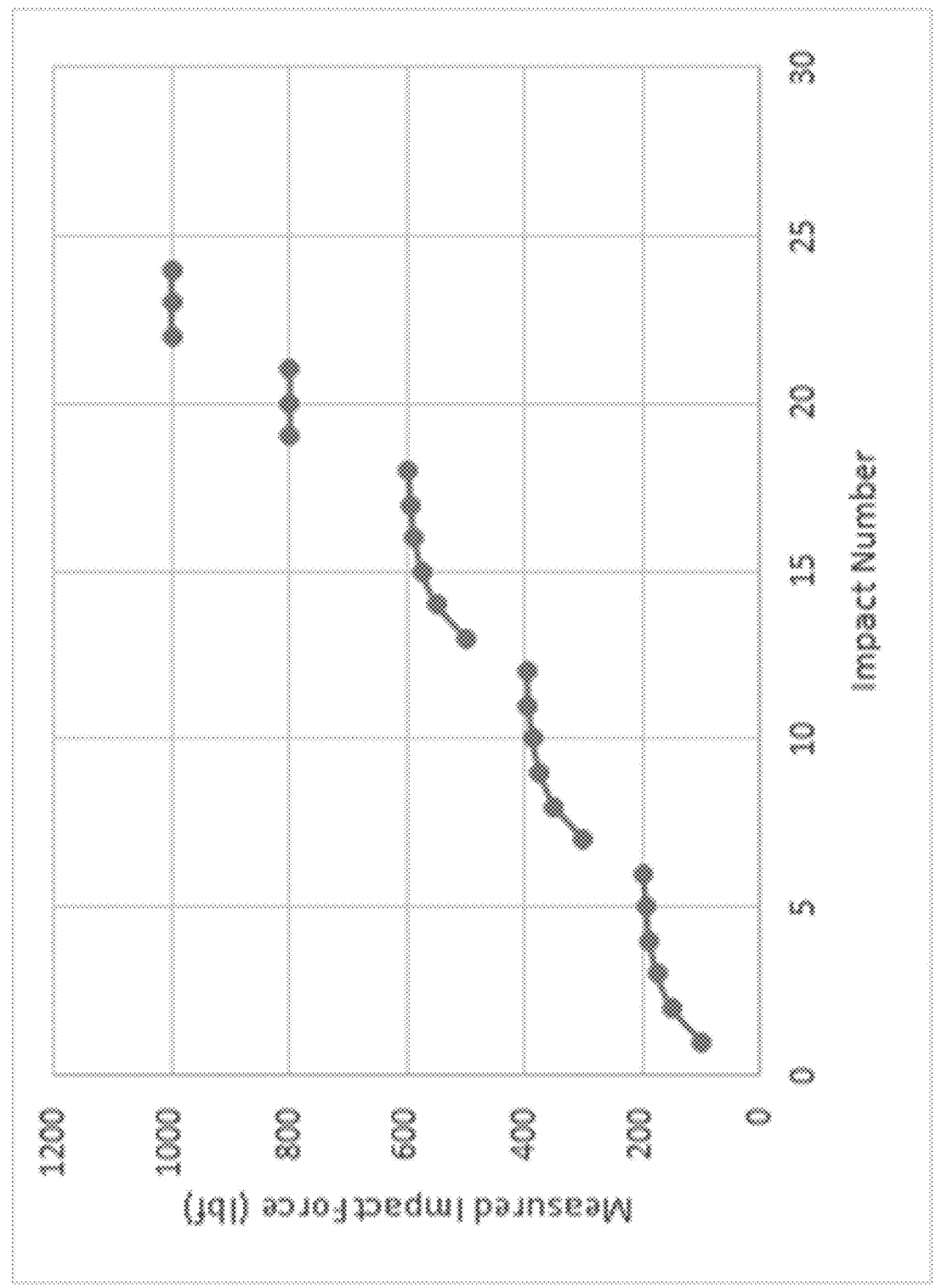

In some embodiments, this relationship may be used to "walk up" the insertion force plot illustrated in FIG. 16, allowing tool 1700 to find the "plateau" of larger and larger impact energies. By increasing the energy linearly, the relationship between measured impact force and cup insertion illustrated in FIG. 18 should hold until the system reaches the non-linear insertion force regime of FIG. 16. When the non-linear regime is reached, a small linear increase in impact energy will not overcome the higher static forces needed to continue to insert the cup. This will result in an almost immediate steady state for the measured impact force (mIF of a force application X is about the same as MIF of a force application X+1). A visual representation of the measured impact force as the impact energy is increased is illustrated in FIG. 19. FIG. 19 illustrates a graph of measured impact force as impact energy is increased. Five impact energy levels are shown, with the last two increases in energy resulting in the cup entering the non-linear portion of the insertion force plot illustrated in FIG. 16.

A procedure for automated impact control/force measurement may include: a) Begin impacts with a static, low energy; b) Record the measured impact force (MIF); c) continue striking until the difference in measured impact force approaches zero (dMIF=>0), inferring that the cup is no longer displacing; d) increase the energy of the impacts by a known, relatively small amount; and e) repeat striking until plateau and increasing energy in a linear fashion until an increase in energy does not result in the relationship shown in FIG. 18. Instead, an increase in energy results in a "step function" in recorded forces, with an immediate steady state. The user could be notified of each increase in energy, allowing a decision by the surgeon to increase the resulting impact force.

Figure 20:
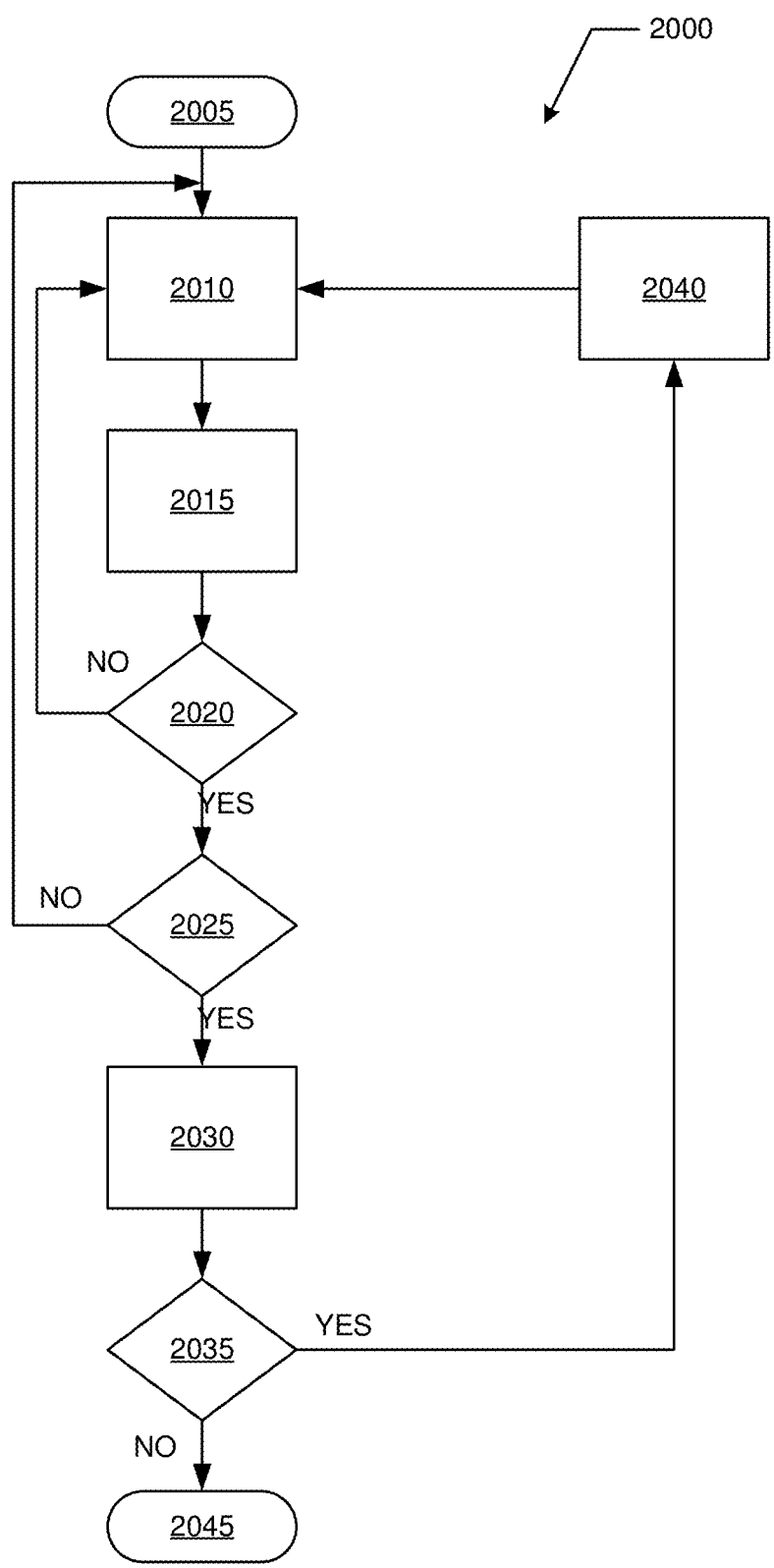

FIG. 20 illustrates a discrete impact control and measurement process 2000. Process 2000 includes step 2005-step 2045. Step 2005 (start) initializes process 2000. Process 2000 advances to a step 2010 to initiate the actuator to impart a known force application with energy X joules. After step 2010, process 2000 advances to step 2015 to measure impact force (MIF). After step 2015, process 2000 tests whether there have been a sufficient number of force applications to properly evaluate/measure a delta MIF (dMIF) between an initial value and a current value. When the test at step 2020 is negative, process 2000 returns to step 2010 to generate another force application event. Process 2000 continues with steps 2010-2020 until the test at step 2020 is affirmative, at which point process 2000 advances to a test at step 2025. Step 2025 tests whether the evaluated dMIF is approaching within a predetermined threshold of zero (that is, MIF(N)−MIF(N−1)=>0 within a desired threshold. When the test at step 2025 is negative, process 2000 returns to step 2010 for produce another force application event and process 2000 repeats steps 2010-2025 until the test at step 2025 is affirmative.

When affirmative, process 2000 advances to a step 2030 and includes a user feedback event to inform a surgeon/observer that the prosthesis is no longer inserting at a given TMIF value. After step 2030, process 2000 may include a test at step 2035 as to whether the user desires to increase the TMIF. Some implementations may not include this test (and either automatically continue until a termination event or the system stops automatically).

In the test at step 2035, the user may choose to have the energy applied from the actuator increased. Process 2000 includes a step 2040 after an affirmative result of the test at step 2035 which increases the current energy applied by the actuator an additional Y joule. After the change of energy at step 2040, process 2000 returns to repeat steps 2010-2035 until the test at step 2035 is negative. At which point, process 2000 advances to an end step 2045 which may include any post-installation processing.

Once the non-linear regime discussed in FIG. 16 is reached, the probability of fracture increases. This is due to the acetabular cup nearing its full insertion depth, with limited incremental displacement from additional blows. This results in larger impact forces that are transmitted to the surrounding bone. Tool 1700 is able to detect when this regime is reached using process 2000, and could generate an alert through the user interface. The implementation of an alert could be performed in a number of different ways. One way would be a warning light and/or tone that would activate when a "step function" increase in measured impact force is detected. More advanced implementations are possible, with the system indicating the increasing probability of fracture as impact energy is increased once a "step function" increase in measured impact force is detected. The increasing risk of fracture could be shown through an LED bar that would illuminate additional lights to correspond to the relative risk, or by computing and displaying a fracture probability directly on the user interface. It should be noted that the cup may not fully seated when the system generates the aforementioned alert. This could be due to cup alignment issues, incorrect bone preparation, or incorrect cup sizing, among other causes. In these instances, the system would generate an alert before the cup is fully inserted, allowing the surgeon to stop and determine the cause of the alert. This may be an additional benefit, allowing detection of an insertion issue before larger impact forces are used. A flowchart for one form of warning implementation is illustrated in FIG. 21.

Figure 21:
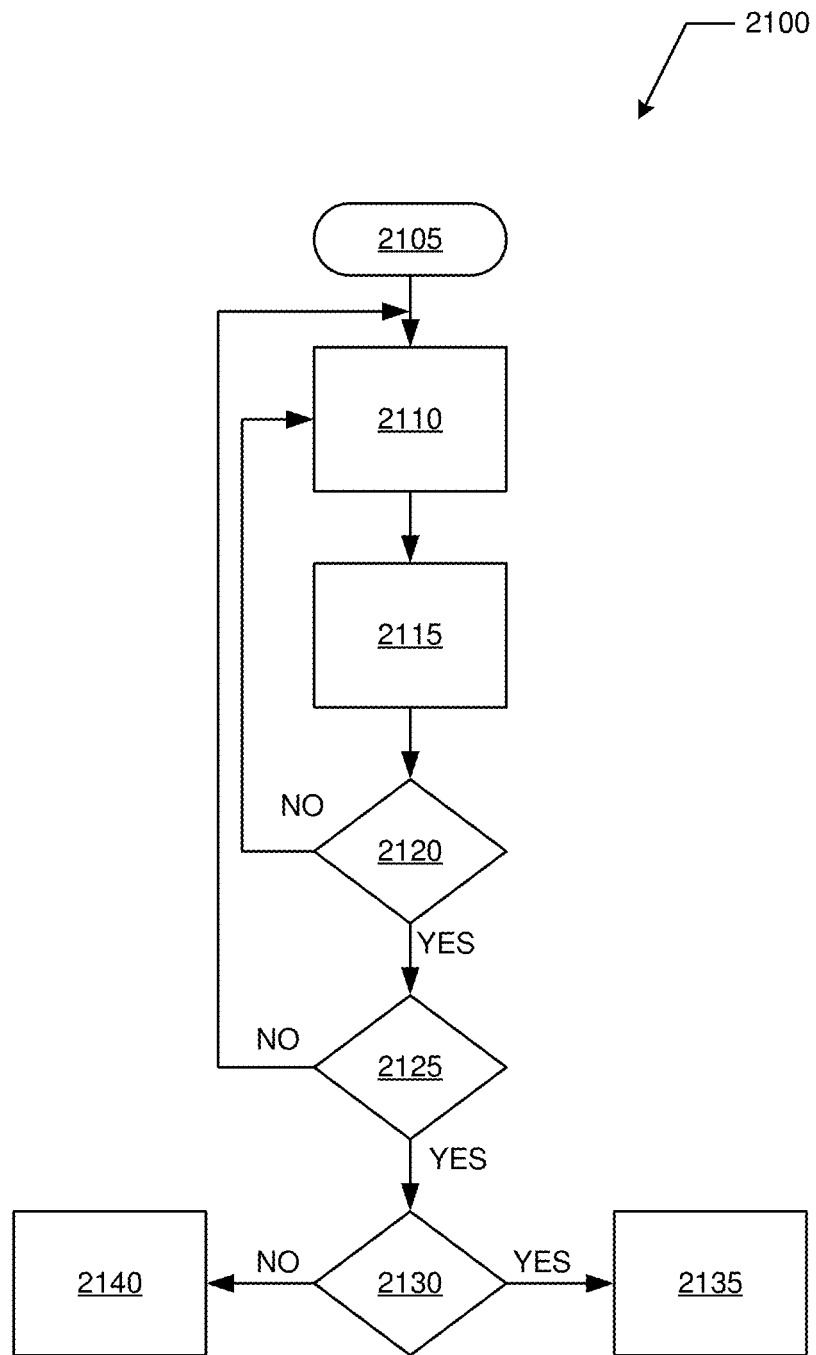

FIG. 21 illustrates a warning process 2100. Process 2100 includes a step 2105-step 2140. Step 2105 (start) initializes process 2100. Process 2100 advances to a step 2110 to initiate the actuator to impart a known force application with energy X joules. After step 2110, process 2100 advances to step 2115 to measure impact force (MIF). After step 2115, process 2100 tests whether there have been a sufficient number of force applications to properly evaluate/measure a delta MIF (dMIF) between an initial value and a current value. When the test at step 2120 is negative, process 2100 returns to step 2110 to generate another force application event. Process 2100 continues with steps 2110-2120 until the test at step 2120 is affirmative, at which point process 2100 advances to a test at step 2125. Step 2125 tests whether the evaluated dMIF is approaching within a predetermined threshold of zero (that is, MIF(N)−MIF(N−1)=>0 within a desired threshold. When the test at step 2125 is negative, process 2100 returns to step 2110 for produce another force application event and process 2100 repeats steps 2110-2125 until the test at step 2125 is affirmative.

When affirmative, process 2100 advances to a step 2130 and includes a warning test event to test whether a first and a last MIF are within measurement error (MIF(0)=MIF(N)?) When the test at step 2130 is affirmative, a warning may be issued. When the test at step 2130 is negative, no warning is issued. There are similarities with process 2000 and process 2100 and some embodiments may combine them.

Improved performance may arise when the device is in the same state before each impact, in that the force applied by the user to the device is relatively consistent. Varying the user's input may influence the measured impact force for a strike, resulting in erroneous resistance curve modeling by the device. In order to minimize the occurrence, the device could actively monitor the force sensor between impacts, looking for a static load before within an acceptable value range. The system could also use the static load measurements directly before a strike as the impact's reference point, allowing relative measurements that reduce the effect of user variation. Even with this step, it is expected that filtering and statistical analysis will need to be performed in order to minimize signal noise.

Figure 22:
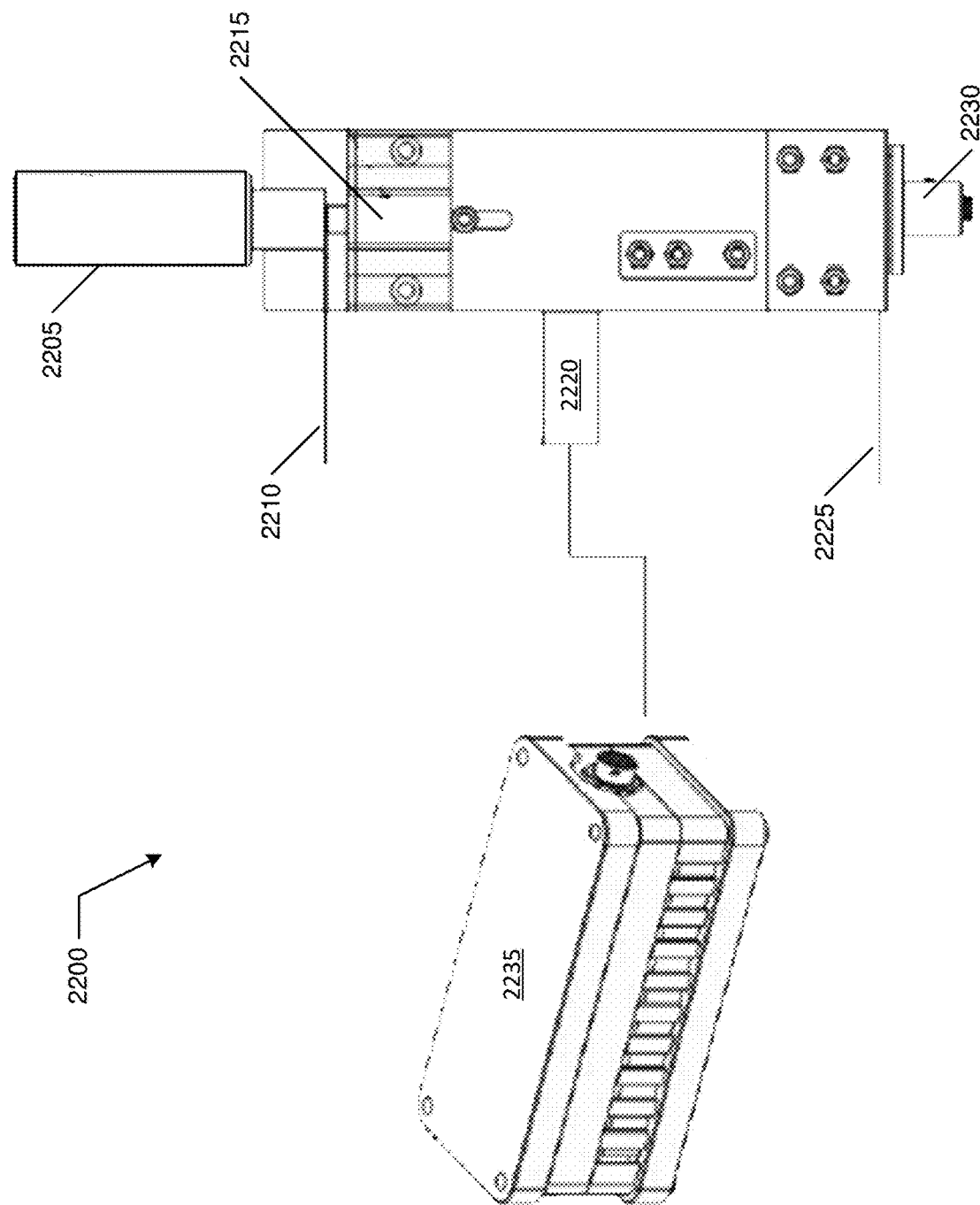
FIG. 22-FIG. 27 illustrate a second specific implementation of the system and method of FIG. 13-FIG. 15.
Figure 23:
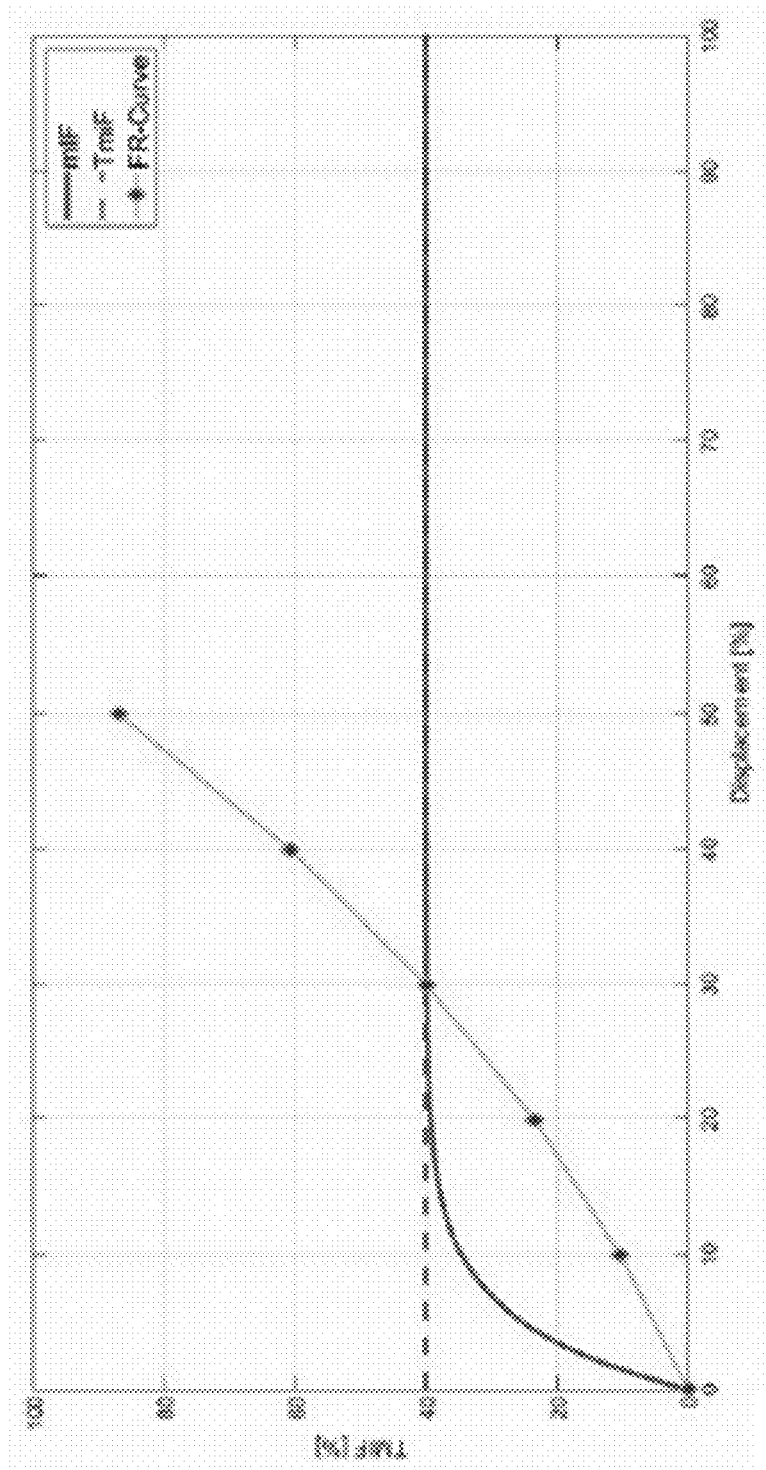
Figure 24:
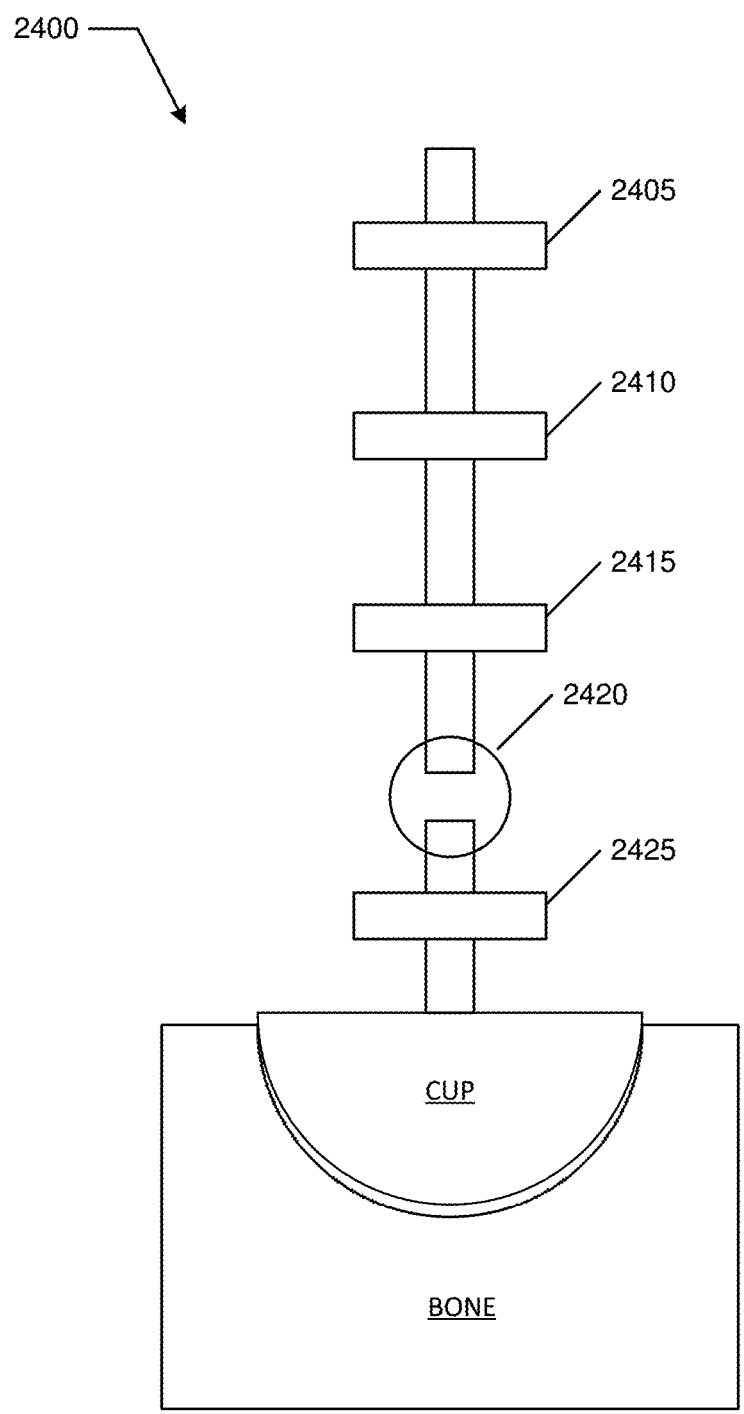

FIG. 22-FIG. 27 illustrate a second specific implementation of the system and method of FIG. 13-FIG. 15; FIG. 22 illustrates a basic force sensor system 2200 for controlled insertion. System 2200 includes a handle 2205, a first force sensor 2210, a shock absorber 2215, a motor 2220, a second force sensor 2225, and impact rod 2230, and a processing unit 2235. A purpose of system 2200 is to use force measurements and estimates to provide cup settlement feedback. A basic configuration of the hardware involved in system 2200 is illustrated in FIG. 22. Important sensors include: Preload sensor 2210, motor current sensor located in PPU 2235; and impaction sensor 2225. Instrumentation of system 2200 either measures or estimates variables illustrated in FIG. 23. FIG. 23 illustrates an FR curve including TmIF and mIF as functions of displacement. FIG. 24 illustrates a generic force sensor tool to access variables of interest in FIG. 23. System 2400, corresponding generally to system 1300 includes a force sensor 2405 (measuring F), a damping mechanism 2410, a current sensor (TmIF estimation and Actuator) function 2415, a vibrating/impacting interface 2420, and a force sensor 2425 (measuring mIF).

The relationship among the three curves in FIG. 23 are able to determine the cup/cavity settlement behavior. mIF can be directly measured by system 2200 as described herein. For example, impaction sensor 2225 may be a force sensor placed in the impacting rod 2230. The impacting rod 2230 receives and transmits impacts directly to the cup. This same impaction force input is sensed by sensor 2225.

TmIF is composed by both preload and actuator force. The preload is measured directly by the force sensor 2210. The actuator force can be estimated by means of current sensing (motor 2220 and PPU 2235) as the torque/force generated by the motor can be related to its electric current.] C. L. Chu, M. C. Tsai, H. Y. Chen, "Torque control of brushless dc motors applied to electric vehicles," in IEEE International Electric Machines and Drives Conference, 2001, pp. 82-87.

Motor 2020 is connected to PPU 2035 where the current sensor is installed. All measurements shall be properly filtered and handled in real-time before any advanced processing takes place. Both low level and advanced real-time processing are executed in PPU 2035 for each sensor. Sensor 2025 needs less processing since this is the direct measurement of mIF. TmIF needs more processing since it is composed by direct measurement of sensor 2010 and estimated force provided by motor 2020. Force estimation is basically data fusion of brushless DC motor current measurements with its electromechanical mathematical model considering mechanism interactions.

Once mIF and TmIF are internally available (to the PPU), the frequency of the actuating mechanism can be changed as a function of these variables. This allows the tool to track the optimal region (the B-Cloud) of the FR-Curve. It is important to note that mIF steady state value depends on current TmIF. In other words, the B-Cloud can be suitably tracked by the combination of both TmIF and mIF as described in the flowchart of FIG. 25.

Figure 25:
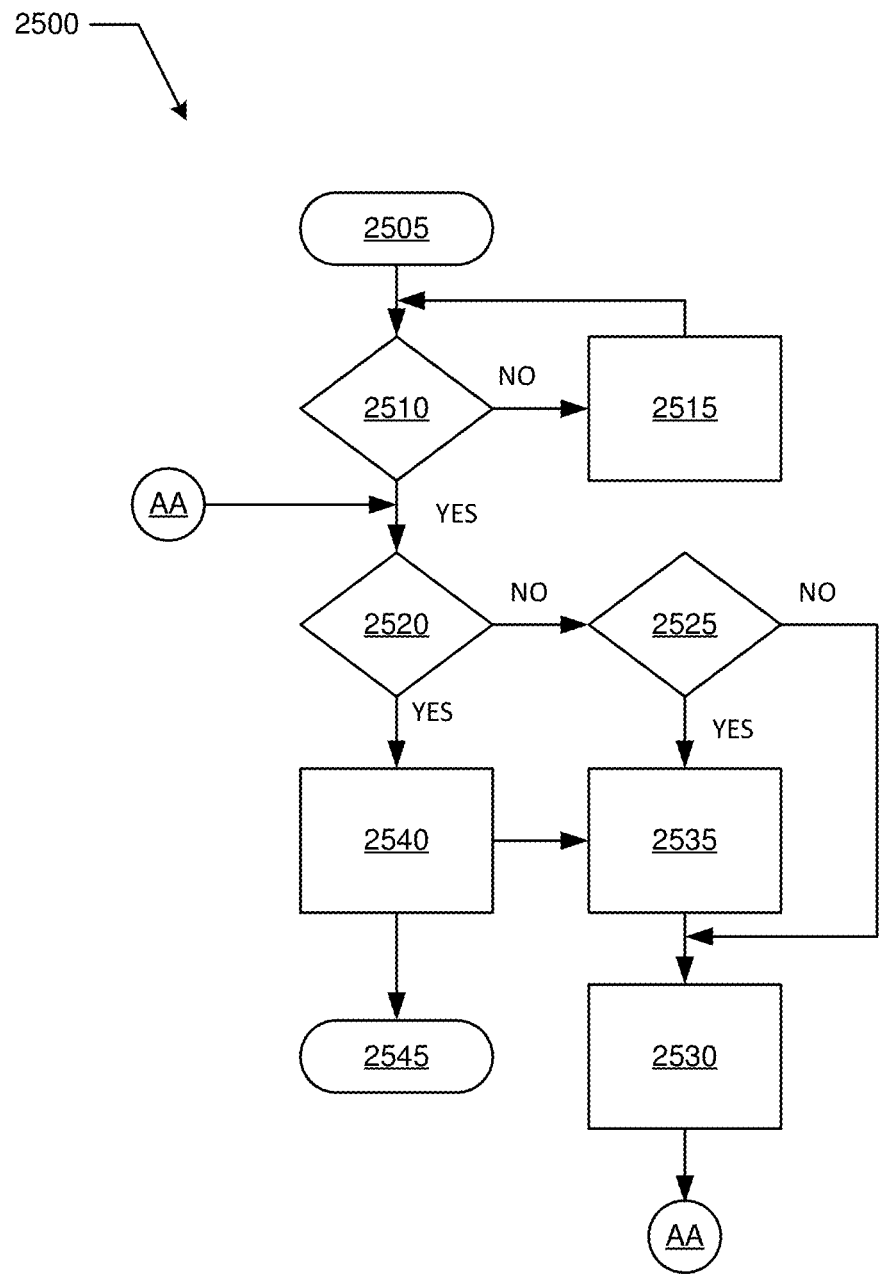

FIG. 25 illustrates a B-cloud tracking process 2500 using TmIF and MIF measurements. Process 2500 includes step 2505-step 2545. Step 2505, a start step, initiates process 2500. After start 2505, process 2500 includes a test step 2510 to determine whether TmIF=mIF. When negative, process 2500 performs a controlled action step 2515 and then returns to step 2510. Process 2500 repeats steps 2510-2515 until the test at step 2510 is affirmative, at which point process 2500 performs a test step 2520 to determine whether the B-cloud is achieved. When the test at step 2520 is negative, process 2500 performs a test step 2525 to determine whether to change the preload. When the test at step 2525 is negative, process 2500 performs a controlled action step 2530 and then branches to AA—to the test at step 2520.

When the test at step 2525 is affirmative, process 2500 queries the surgeon at step 2535 as to changing the preload. In response to surgeon consultation step 2535, process 2500 performs controlled action step 2530. Process 2500 repeats steps 2520-2535 until the test at step 2520 is affirmative. When affirmative, process 2500 performs a stop insertion step 2540 and may either ask surgeon at step 2530 and/or conclude process 2500 by performing an end step 2545.

Figure 26:
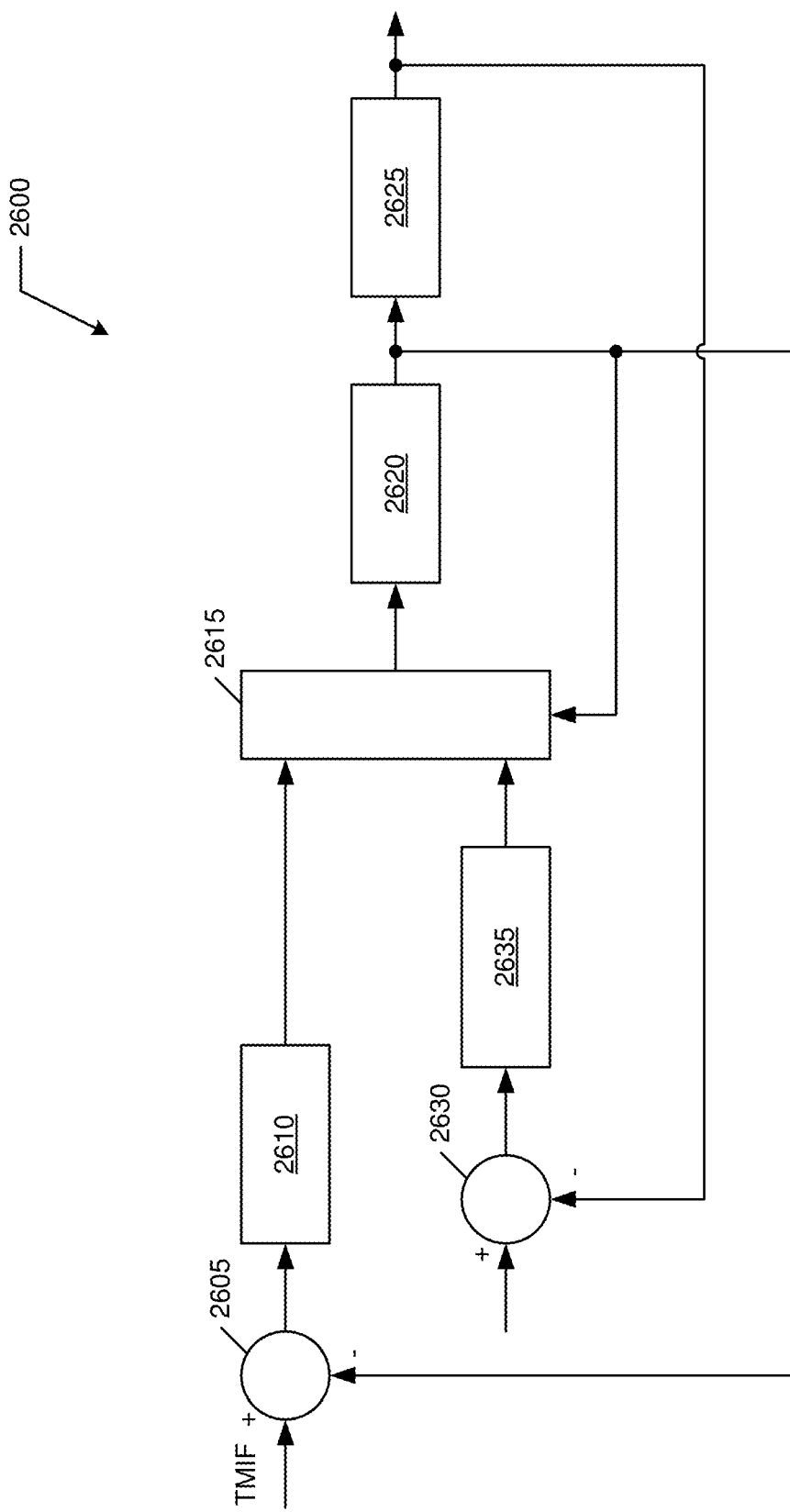

Process 2500 begins when the cup is preloaded against the cavity. It may be triggered by force threshold or button press. Current TmIF and mIF are constantly compared and regulated to be equal according to an internal control system when they are not able to converge easily. The control system is detailed in FIG. 26. FIG. 26 illustrates a control system 2600 for the "controlled action" referenced in FIG. 25.

Control system 2600 includes a set of processing blocks, real objects, computed signals and raw measurement and computed signals selectively responsive to input force and input frequency commands. System 2600 includes a feedback block 2605, a Bcloud regulator block 2610, a control selector 2615, a device/cavity/cup interaction assessment 2620, an FR curve estimator 2625, a feedback block 2630, and a performance pursuit block 2635.

Feedback block 2605 compares TMIF against an output (input force command and mIF) of block 2620. When/If there is an Input Force error at block 2605, B cloud Regulator provides a first input frequency command f1 in response to the IF error. Feedback block 2630 compares a maximum feasible gain against a cup/cavity gain estimate from FR estimator 2625. When/if there is a gain error, performance pursuit 2635 takes this gain error and produces a second input frequency command. Control selector 2615 accepts both input frequency commands and selects one and provides it to the device/cavity/cup interaction 2620. Interaction 2620 produces input force command and mIF to FR estimator 2625, to selector 2615, and to feedback block 2605.

As the achievement of the B-Cloud is an objective, it is also constantly verified if it was achieved. However, the achievement of the B-Cloud is constrained to the value of the force source measured by TmIF. When the B-Cloud is not achieved, it is evaluated if there is need of pre-load increase or not (i.e. the actuator alone would be able to increase TmIF). In case of additional pre-load needed, the device asks the surgeon to increase the pre-load. The control system keeps running to make mIF track TmIF in an optimized way. The insertion stops automatically when the B-Cloud is achieved for the first time. A reference value inside the B-Cloud can be adjusted by the surgeon if she realizes based on its visual feedback that additional or less insertion force is necessary.

There are possible exceptions related to abnormal or unexpected cup/cavity behavior. As a cup/cavity which needs too much pre-load or much more force than some actuators are able to achieve. For this reason the "B-Cloud regulation" block 2610 in FIG. 26 may be implemented in two distinct ways: a BMD3 device alone (curve 2705 in FIG. 27—mIF strong BMD3); or hybrid BMD3/BMD4 devices combined (curve 2710 with "weak" mIF BMD3 switched to BMD4-hybrid or discrete devices).

Figure 27:
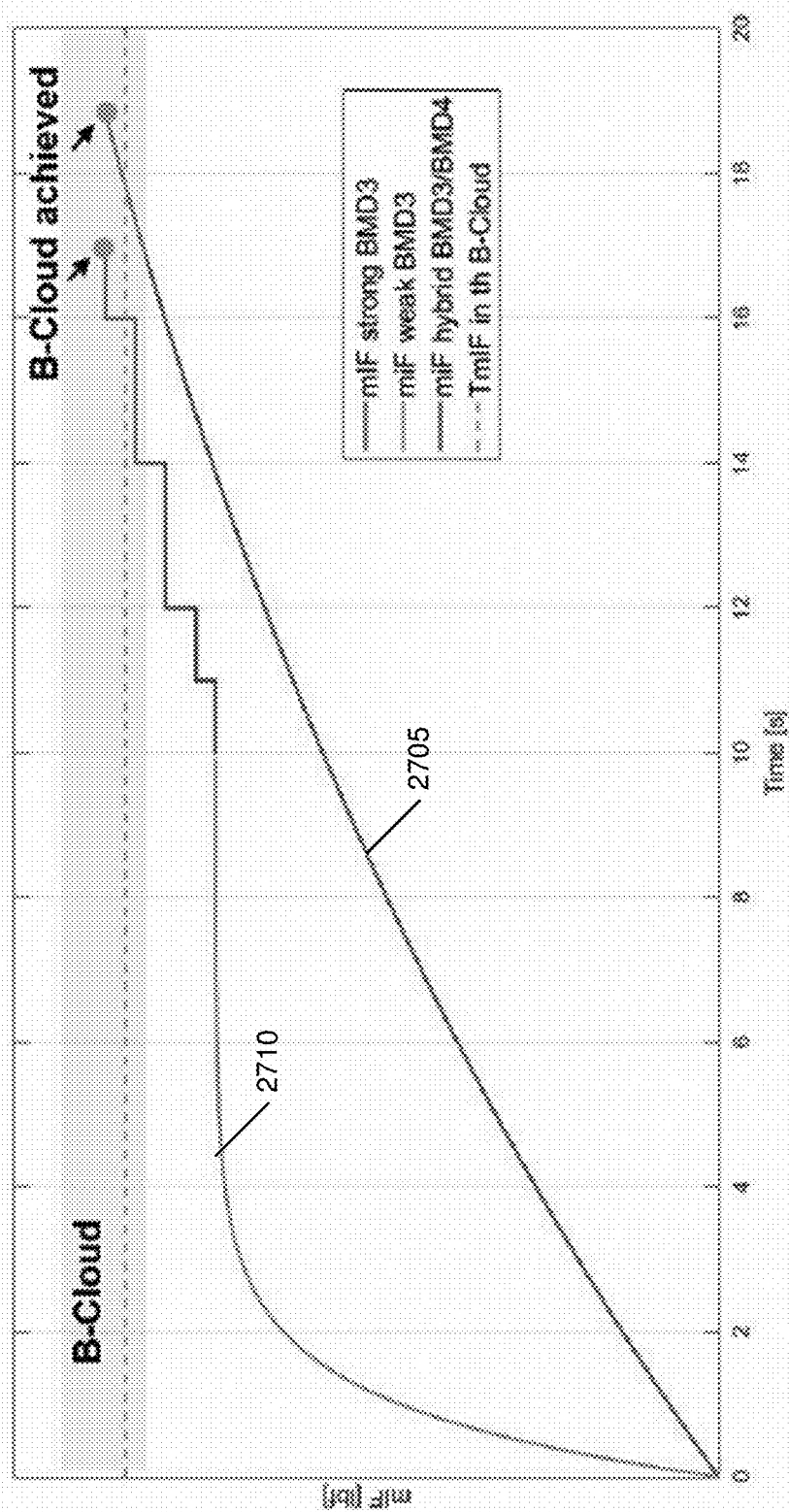

FIG. 27 illustrates possible B-cloud regulation strategies. A value on the B-Cloud is taken as reference for the B-Cloud regulator, this value is expressed by the dashed line in 27. In the case of a BMD3 able to perform the job alone, it can be achieved smoothly. In the case that BMD3 does not have sufficient power to accomplish the task, it switches to BMD4 which provides incremental impacts proportional to the difference between mIF and TmIF. Progressive BMD4 impacts change its amplitude following $K_{BMD4}(m_{IF}-T_{mIF})$, while $K_{BMD}$ is a parameter which has to be determined experimentally.

Estimation of the force provided by the motor

Figure 28:
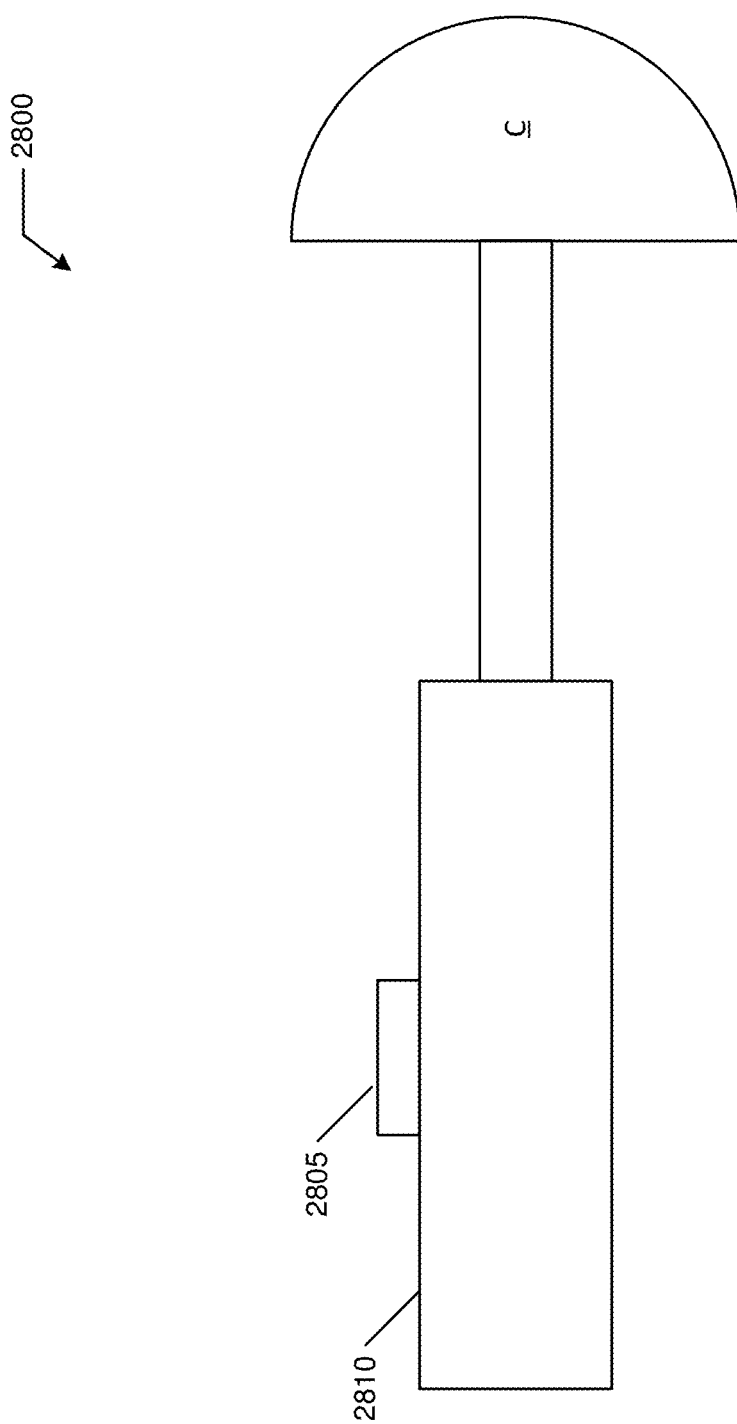
FIG. 28 illustrates a generalized BMD including real-time invasive sense measurement.

A reliable and feasible way to determine the amount of force made available by the actuator is by means of electrical current measurement. The accuracy and sizes involved in our application would make difficult the installation of force/torque sensors for motors and piezo transducers, which are the basic types of actuators used in BMD3 and BMD4 devices. However, electrical current drawn by these actuators is related to the force produced by them. In other words, the force produced can be understood as a function of the electrical current. This idea is largely in engineering. Our proposed solution would make use of estimators (e.g. Kalman filter) which relate the mathematical model of the electromechanical actuator fused with measured values of the electrical current to provide the force output generated in real-time by the actuator FIG. 28 illustrates a generalized BMD 2800 including real-time invasive sense measurement. BMD 2800 includes one or more micro-electro-mechanical systems (MEMS) 2805 to measure real-time invasive sense measurement for BMD 2800. MEMS 2805 are secured to BMD 2800, such as by for example, an attachment or other coupling to a handle 2810 of BMD 2800. As illustrated, BMD 2800 includes an acetabular cup C for installation, though other systems may be used for different prosthetics.

During a procedure, MEMS 2805 provides real-time parametric evaluation of relevant information that may be needed or desired by an operator of handle 2810. For example, an orientation and seatedness of cup C may be evaluated in real-time to allow the operator to suspend operation when a desired orientation and/or seatedness has been achieved. MEMS 2805 may evaluate orientation, displacement depth, seatedness, using a range of potential sensing systems, including force, acceleration, vibration, acoustics, and other information. Just as an interaction between cup C and an installation site may produce an FR curve as described herein, various interactions of BMD 2800 or one or more components of BMD 2800 (e.g., cup C) with the installation site may produce characteristic profiles or "prints" that change during the real-time operation. Monitoring these parametric prints in true real-time may provide the operator with helpful information that is not available with a series of pre-process measurement and post-process measurement.

The force parameter has been described herein. Other parameters of acceleration, vibration, acoustic, and the like information may provide helpful information as well by including appropriate sensing structures for acceleration, vibration, acoustic, and the like. In the case of an installation depth of an acetabular cup, these parameters may help the operator to identify and differentiate between the three zones: too little seatedness zone, sweet zone, and fracture-risk zone. The specifics by which these zones are detected and identified are likely to be different, however.

BMD 2800, by appropriate selection of multiple sensing systems in MEMS 2805, may improve performance by providing a logical product of different parametric evaluations. That is, while any single parameter of force, acceleration, vibration, acoustic, or the like may offer improved performance, having multiple different sensors all operating in true real-time to cross/double check can offer improved performance.

In some cases, a system may not identify that the prosthesis is in the sweet zone unless multiple parametric systems concur. In other cases, it may be that a first to detect a fracture-risk zone may result in suspension or termination of the installation process. Or that all systems must indicate adequate seatedness before stopping (possibly adding a further condition of providing no fracture risk detection).

Even without automatic detection of these zones, the combined information may useful to the operator in evaluating how to proceed with the installation to help maximize the desired orientation and seatedness without unnecessarily risking fracture.

Other procedures besides cup installation (e.g., installing a different type of prosthesis), other processes other than prosthesis installation (e.g., assembling a modular prosthesis), and other invasive operations (e.g., bone preparation), and other medical interventions that do not relate to prosthesis preparation, installation, and assembly may all benefit from providing true real-time analysis and feedback.

Feedback from a MEMS sensing system may be accomplished by one or more of a display or indicator on or integrated with the device, and/or an associated module in communication with the MEMS sensing system/display, a robot or navigation system in communication with the MEMS sensing system and/or an associated module.

The system and methods above have been described in general terms as an aid to understanding details of preferred embodiments of the present invention. In the description herein, numerous specific details are provided, such as examples of components and/or methods, to provide a thorough understanding of embodiments of the present invention. Some features and benefits of the present invention are realized in such modes and are not required in every case. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

It will also be appreciated that one or more of the elements depicted in the drawings/figures can also be implemented in a more separated or integrated manner, or even removed or rendered as inoperable in certain cases, as is useful in accordance with a particular application.

Additionally, any signal arrows in the drawings/Figures should be considered only as exemplary, and not limiting, unless otherwise specifically noted. Combinations of components or steps will also be considered as being noted, where terminology is foreseen as rendering the ability to separate or combine is unclear.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

The invention claimed is:

1. An apparatus for insertion of a prosthesis into a cavity in a portion of bone, the prosthesis having a prosthesis profile, the prepared cavity having a cavity profile with the cavity profile configured, responsive to the prosthesis profile, to retain the prosthesis within the prepared cavity using a press fit fixation, comprising:
an insertion device providing an insertion force to the prosthesis, said insertion force including an initial prosthesis insertion act with said insertion device to a subsequent prosthesis insertion act with said insertion device; and
a sensing system physically coupled to said insertion device configured to provide a parametric evaluation of an extractive force of an interface between the prosthesis and the cavity during said period;
wherein said initial prosthesis insertion action includes an initial applied force;
wherein said subsequent prosthesis insertion action includes a subsequent applied force;
wherein said parametric evaluation includes a first quantification of a prosthesis response force subsequent to said initial applied force and further includes a second quantification of said prosthesis response force subsequent to said subsequent applied force; and
wherein said parametric evaluation further includes a comparison of one or more of said forces.

2. The apparatus of claim 1 wherein said insertion device includes a prosthesis insertion device and wherein said parametric evaluation includes a quality of a seatedness and a metric of a fracture-risk of the portion of bone; and
wherein said quality of seatedness includes said extractive force of said interface.

3. The apparatus of claim 1 wherein an applied force having a first magnitude is applied to said insertion device for inserting the prosthesis into the cavity, further comprising:
a device sensor configured to measure a magnitude of a measured impact force within said insertion device responsive to an application of said applied force to said insertion device.

4. The apparatus of claim 3 wherein said first magnitude of said applied force includes a predetermined applied force having a predetermined first magnitude.

5. The apparatus of claim 4 further comprising an applied force sensor configured to measure said first magnitude of said applied force.

6. The apparatus of claim 1 wherein said insertion force includes a vibratory insertion force.

7. The apparatus of claim 1 wherein said insertion force includes a periodic controlled impaction insertion force.

8. The apparatus of claim 1 further including a robot and wherein said insertion force includes a continuous insertion force provided by said robot.

9. The apparatus of claim 1 wherein the prosthesis includes an acetabular cup.

10. The apparatus of claim 1 wherein said parametric evaluation of said extractive force includes a response of the prosthesis within the cavity to said insertion force.

11. The apparatus of claim 10 wherein said insertion force includes an applied force directed to the prosthesis and wherein said response includes a force response of the prosthesis within the cavity.

12. The apparatus of claim 1 wherein said sensing system further comprises an applied force sensor configured to quantify said applied forces.

13. The apparatus of claim 1 wherein said sensing system further comprises a response sensor configured to produce said quantifications of said prosthesis response forces.

14. The apparatus of claim 12 wherein said sensing system further comprises a response sensor configured to produce said quantifications of said prosthesis response forces.

15. The apparatus of claim 1 wherein said comparison includes a first comparison of said first quantification to said initial applied force and further includes a second comparison of said second quantification to said subsequent applied force.

16. The apparatus of claim 1 wherein said subsequent applied force is about equal to said subsequent applied force and wherein said comparison includes a first comparison of said second quantification to said first quantification.

17. An apparatus for an insertion of a prosthesis into a cavity in a portion of bone, the prosthesis having a prosthesis profile, the prepared cavity having a cavity profile with the cavity profile configured, responsive to the prosthesis profile, to retain the prosthesis within the prepared cavity using a press fit fixation, comprising:
means for applying an insertion force to the prosthesis, said insertion force directing the insertion of the prosthesis into the cavity; and
means, coupled to said means for applying said insertion force and responsive to said insertion force, for determining a parametric evaluation of an extractive force of an interface between the prosthesis and the cavity during an application of said insertion force to the prosthesis;
wherein said parametric evaluation includes a comparison of quantified forces.

18. The apparatus of claim 17 further comprising:
means, cooperating with said means for determining said parametric evaluation and responsive to said parametric evaluation during said application of said insertion force to the prosthesis, for assessing a quality of seatedness of the prosthesis within the cavity.

19. The apparatus of claim 17 wherein said means for determining includes a set of two or more sensors quantifying a set of forces in said means for applying.

20. The apparatus of claim 18 wherein said means for determining includes a set of two or more sensors quantifying a set of forces in said means for applying.

* * * * *